(12) United States Patent
Topalian et al.

(10) Patent No.: US 6,982,168 B1
(45) Date of Patent: Jan. 3, 2006

(54) IMMORTAL HUMAN PROSTATE EPITHELIAL CELL LINES AND CLONES AND THEIR APPLICATIONS IN THE RESEARCH AND THERAPY OF PROSTATE CANCER

(75) Inventors: Suzanne L. Topalian, Brookeville, MD (US); W. Marston Linehan, Rockville, MD (US); Robert K. Bright, Portland, OR (US); Cathy D. Vocke, Germantown, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/913,770

(22) PCT Filed: Jan. 30, 1997

(86) PCT No.: PCT/US97/01430

§ 371 (c)(1),
(2), (4) Date: Sep. 22, 1997

(87) PCT Pub. No.: WO97/28255

PCT Pub. Date: Aug. 7, 1997

Related U.S. Application Data
(60) Provisional application No. 60/011,042, filed on Feb. 2, 1996.

(51) Int. Cl.
*C12N 15/85* (2006.01)

(52) U.S. Cl. .................. 435/325; 435/366; 435/371; 435/384; 435/385; 435/386

(58) Field of Classification Search .............. 424/184.1, 424/277.1, 93.7; 435/7.23, 325, 366, 378
See application file for complete search history.

(56) References Cited

U.S. PATENT DOCUMENTS

| | | | |
|---|---|---|---|
| 5,026,637 A | 6/1991 | Soule et al. | 435/29 |
| 5,376,542 A | 12/1994 | Schlegal | 435/172.2 |
| 5,436,152 A | 7/1995 | Soule et al. | 435/240.2 |
| 5,443,954 A | 8/1995 | Reddel et al. | 435/7.21 |
| 5,462,870 A | 10/1995 | Chopra | 435/240.2 |
| 5,576,206 A | 11/1996 | Schlegel | 435/240.2 |
| 5,716,830 A | 2/1998 | Webber et al. | 435/6 |
| 5,824,488 A | * 10/1998 | Webber et al. | 435/7.23 |

FOREIGN PATENT DOCUMENTS

| | | |
|---|---|---|
| WO | WO 92/16645 | 10/1992 |
| WO | WO 95/29990 | 11/1995 |
| WO | WO 95/29994 | 11/1995 |

OTHER PUBLICATIONS

Chiarello, E, Oncogene 16: 541–545, 1998.*
Kelemen. Genes Chromosomes Cancer 11:195–198, 1994.*
Drexler. Leukemia & Lymphoma 9:1–25, 1993.*
Embleton, Immunol. Ser. 23:181–207, 1984.*
Heu, In: Tissue Culture Meth & Applications, Kruse & Patterson, Eds, p. 764, 1973.*
Mustafa O. Intl. J. Oncol. 8(5):883–888, 1996.*
ATCC Catalogue of Cell Lines & Hybridomas, 6th edition, pp. 145 and 222, 1988.*
Bernardino et al. "Characterization of Chromosome changes in two human prostatic charcinoma cell lines (PC–3 and DU 145) using chromosome painting and comparative genomic hybridization" Cancer Genet. Cytogenet. vol. 96, pp. 123–128, 1997.*
Freshney, Culture of Animal Cells, A manual of basic technique chapter 13, p. 130, 1983.*
Smith, R. T. "Cancer and the immune system" Clinical Immunology. vol. 41 No. 4, pp. 841–850, Aug. 1994.*
McInerney J. M et al. Gene Therapy 7(8): 653–63, 2000.*
Parda et al, "Neoplastic Transformation of a Human Prostate Epithelial Cell Line by the v–Ki–ras Oncogene", *The Prostate* 23:91–98 (1993).
Hayward et al, "Establishment and Characterization of an Immortalized But Non–Transformed Human Prostate Epithelial Cell Line: BPH–1", *In Vitro Cell Dev. Biol.* 31A:14–24, Jan. 1995.
Castagnetta et al, "Prostate Long–Term Epithelial Cell Lines", *Annals of The New York Academy of Sciences*, vol. 595, pp. 149–164, 1990.
Boudou et al, "Distinct Androgen 5a–Reduction Pathways in Cultured Fibroblasts and Immortalized Epithelial Cells From Normal Human Adult Prostate", *The Journal of Urology*, vol. 152, 226–231, Jul. 1994.
Narayan et al, "Establishment and Characterization of a Human Primary Prostatic Adenocarcinoma Cell Line (ND–1)", *The Journal of Urology*, vol. 148, 1600–1604, Nov. 1992.
Rhim et al, "Stepwise immortalization and transformation of adult human prostate epithelial cells by a combination of HPV–18 and v–Ki–ras", *Proc. Natl. Acad. Sci. USA*, vol. 91, pp. 11874–11878, Dec. 1994.

(Continued)

*Primary Examiner*—Susan Ungar
*Assistant Examiner*—Minh-Tam Davis
(74) *Attorney, Agent, or Firm*—Leydig, Voit & Mayer, Ltd.

(57) ABSTRACT

The present invention relates to immortalized, malignant, human, adult prostate epithelial cell lines or cell lines derived therefrom useful in the diagnosis and treatment of prostate cancer. More particularly, the present invention relates to cloned, immortalized, malignant, human, adult prostate epithelial cell lines and uses of these cell lines for the diagnosis and treatment of cancer. Furthermore, the present invention provides for the characterization of said cell lines through the analysis of specific chromosomal deletions.

21 Claims, 6 Drawing Sheets

OTHER PUBLICATIONS

Cussenot et al, "Immortalization of Human Adult Normal Prostatic Epithelial Cells By Liposomes Containing Large T–SV40 Gene", *The Journal of Urology*, vol. 143, 881–886, Sep. 1991.

Weijerman et al, "Lipofection–mediated Immortalization of Human Prostate Epithelial Cells of Normal and Malignant Origin Using Human Papillomavirus Type 18 DNA[1]", *Cancer Research* 54, 5579–5583, Nov. 1, 1994.

Emmert–Buck et al, "Allelic Loss on Chromosome 8p12–21 in Microdissected Prostatic Intraepithelial Neoplasia", *Cancer Research* 55, 2959–2962, Jul. 15, 1995.

Bright et al, "Generation and Characterization of Long–Term Human Prostate Epithelial Cell Lines From Primary Cancer Specimens", Abstract Keystone Symposia Presentation, Feb. 2, 1996.

Bright et al, "Generation and genetic characterization of immortal human prostate epithelial cell lines derived from primary cancer specimens", *Cancer Research* 57(5):995–1002, Mar. 1, 1997.

* cited by examiner

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 19 BASE PAIRS
      (B) TYPE: NUCLEIC ACID
      (C) STRANDEDNESS: SINGLE
      (D) TOPOLOGY: LINEAR (ii) SEQUENCE DESCRIPTION: SEQ ID NO:1:

```
GAGCCCAGAC AGGCTGGAA                                                19
```

(2) INFORMATION FOR SEQ ID NO:2:

(i) SEQUENCE CHARACTERISTICS:
      (A) LENGTH: 21 BASE PAIRS
      (B) TYPE: NUCLEIC ACID
      (C) STRANDEDNESS: SINGLE
      (D) TOPOLOGY: LINEAR (ii) SEQUENCE DESCRIPTION: SEQ ID NO:2:

```
ACTTTTCTGG CCAAACTCCT G                                             21
```

(2) INFORMATION FOR SEQ ID NO:3:

(i) SEQUENCE CHARACTERISTICS:
      (A) LENGTH: 20 BASE PAIRS
      (B) TYPE: NUCLEIC ACID
      (C) STRANDEDNESS: SINGLE
      (D) TOPOLOGY: LINEAR (ii) SEQUENCE DESCRIPTION: SEQ ID NO:3:

```
CAGGTGGGAA AACTGAGGGA                                               20
```

(2) INFORMATION FOR SEQ ID NO:4:

(i) SEQUENCE CHARACTERISTICS:
      (A) LENGTH: 22 BASE PAIRS
      (B) TYPE: NUCLEIC ACID
      (C) STRANDEDNESS: SINGLE
      (D) TOPOLOGY: LINEAR (ii) SEQUENCE DESCRIPTION: SEQ ID NO:4:

```
AGCAACTGTC AACATATTGC TC                                            22
```

(2) INFORMATION FOR SEQ ID NO:5:

(i) SEQUENCE CHARACTERISTICS:
      (A) LENGTH: 19 BASE PAIRS
      (B) TYPE: NUCLEIC ACID
      (C) STRANDEDNESS: SINGLE
      (D) TOPOLOGY: LINEAR (ii) SEQUENCE DESCRIPTION: SEQ ID NO:5:

```
GCCCAAAGAG GAGAATAAA                                                19
```

(2) INFORMATION FOR SEQ ID NO:6:

(i) SEQUENCE CHARACTERISTICS:
      (A) LENGTH: 18 BASE PAIRS
      (B) TYPE: NUCLEIC ACID
      (C) STRANDEDNESS: SINGLE (D) TOPOLOGY: LINEAR (ii) SEQUENCE DESCRIPTION: SEQ ID NO:6:

CTGTTTCCAC ACCGAAGC                                                    18

(2) INFORMATION FOR SEQ ID NO:7:

(i) SEQUENCE CHARACTERISTICS:
            (A) LENGTH: 20 BASE PAIRS
            (B) TYPE: NUCLEIC ACID
            (C) STRANDEDNESS: SINGLE
            (D) TOPOLOGY: LINEAR (ii) SEQUENCE DESCRIPTION: SEQ ID NO:7:

GCAGTAGTGC CGCAGTTTCA                                                  20

(2) INFORMATION FOR SEQ ID NO:8:

(i) SEQUENCE CHARACTERISTICS:
            (A) LENGTH: 20 BASE PAIRS
            (B) TYPE: NUCLEIC ACID
            (C) STRANDEDNESS: SINGLE
            (D) TOPOLOGY: LINEAR (ii) SEQUENCE DESCRIPTION: SEQ ID NO:8:

TGCAATTCAT CTTCCTTTCT                                                  20

(2) INFORMATION FOR SEQ ID NO:9:

(i) SEQUENCE CHARACTERISTICS:
            (A) LENGTH: 22 BASE PAIRS
            (B) TYPE: NUCLEIC ACID
            (C) STRANDEDNESS: SINGLE
            (D) TOPOLOGY: LINEAR (ii) SEQUENCE DESCRIPTION: SEQ ID NO:9:

AAATACCGAG ACTCACACTA TA                                               22

(2) INFORMATION FOR SEQ ID NO:10:

(i) SEQUENCE CHARACTERISTICS:
            (A) LENGTH: 21 BASE PAIRS
            (B) TYPE: NUCLEIC ACID
            (C) STRANDEDNESS: SINGLE
            (D) TOPOLOGY: LINEAR (ii) SEQUENCE DESCRIPTION: SEQ ID NO:10:

GCTAATCAGG GAATCACCCA A                                                21

(2) INFORMATION FOR SEQ ID NO:11:

(i) SEQUENCE CHARACTERISTICS:
            (A) LENGTH: 22 BASE PAIRS
            (B) TYPE: NUCLEIC ACID
            (C) STRANDEDNESS: SINGLE
            (D) TOPOLOGY: LINEAR (ii) SEQUENCE DESCRIPTION: SEQ ID NO:11:

ACATAGGCTG GAGAGTCACA GG                                               22

(2) INFORMATION FOR SEQ ID NO:12:

(i) SEQUENCE CHARACTERISTICS:
            (A) LENGTH: 22 BASE PAIRS
            (B) TYPE: NUCLEIC ACID
            (C) STRANDEDNESS: SINGLE
            (D) TOPOLOGY: LINEAR (ii) SEQUENCE DESCRIPTION: SEQ ID NO:12:

GGATGAGGCT CAGCACACAA GC                                        22

(2) INFORMATION FOR SEQ ID NO:13:

(i) SEQUENCE CHARACTERISTICS:
        (A) LENGTH: 18 BASE PAIRS
        (B) TYPE: NUCLEIC ACID
        (C) STRANDEDNESS: SINGLE
        (D) TOPOLOGY: LINEAR (ii) SEQUENCE DESCRIPTION: SEQ ID NO:13:

TAGATGTTAC CATTTCAC                                             18

(2) INFORMATION FOR SEQ ID NO:14:

(i) SEQUENCE CHARACTERISTICS:
        (A) LENGTH: 18 BASE PAIRS
        (B) TYPE: NUCLEIC ACID
        (C) STRANDEDNESS: SINGLE
        (D) TOPOLOGY: LINEAR (ii) SEQUENCE DESCRIPTION: SEQ ID NO:14:

GATTAGATCT TGGATCAG                                             18

(2) INFORMATION FOR SEQ ID NO:15:

(i) SEQUENCE CHARACTERISTICS:
        (A) LENGTH: 20 BASE PAIRS
        (B) TYPE: NUCLEIC ACID
        (C) STRANDEDNESS: SINGLE
        (D) TOPOLOGY: LINEAR (ii) SEQUENCE DESCRIPTION: SEQ ID NO:15:

TCCCAGATCG CTCTACATGA                                           20

(2) INFORMATION FOR SEQ ID NO:16:

(i) SEQUENCE CHARACTERISTICS:
        (A) LENGTH: 20 BASE PAIRS
        (B) TYPE: NUCLEIC ACID
        (C) STRANDEDNESS: SINGLE
        (D) TOPOLOGY: LINEAR (ii) SEQUENCE DESCRIPTION: SEQ ID NO:16:

CACAGCTTCA GAAGTCACAG                                           20

IMMORTAL HUMAN PROSTATE EPITHELIAL CELL LINES AND CLONES AND THEIR APPLICATIONS IN THE RESEARCH AND THERAPY OF PROSTATE CANCER

This application is the national phase of PCT International Application No. PCT/US97/01430 filed Jan. 30, 1997 which is a continuation-in-part of U.S. Application Ser. No. 60/011,042 filed Feb. 2,1996.

FIELD OF THE INVENTION

The present invention relates to immortalized, malignant, human adult prostate epithelial cell lines. The invention also relates to single cell clones of these lines. The invention further relates to immortalized, malignant, human, adult prostate epithelial cell lines and clones characterized by analysis of allelic loss of heterozygosity. More particularly, the invention relates to pairs of autologous normal and malignant prostate epithelial cell lines and clones and their applications in research. The invention also relates to the uses of the cells in the diagnosis and treatment of prostate cancer.

BACKGROUND OF THE INVENTION

Difficulty in establishing long term human prostatic cancer cell lines in vitro has impeded progress toward the understanding of prostate tumorigenesis and the development of new therapies for prostate cancer. To date only four prostate cancer cell lines, initiated from metastatic lesions, have provided the basis for the majority of in vitro experiments concerning the biological and molecular events regulating prostate tumorigenesis. Accordingly, there is an enormous academic, diagnostic, and therapeutic need for established long-term prostate cancer cell cultures.

In recent years, prostate cancer has emerged as the most commonly diagnosed cancer in men in the United States. In this year alone, new cases of prostate cancer are estimated to approach 300,000 with over 40,000 deaths, resulting in a cancer mortaility rate second only to lung cancer (1). Although prostate cancer mortality commonly results from metastatic disease, nearly 60% of newly diagnosed patients present with localized primary tumors. Surgery and radiation therapy are often effective in treating localized disease, but disseminated metastatic disease is largely untreatable. Despite considerable scientific effort there is still relatively little known about the biological events causing the initiation and progression of prostate cancer. The development of new strategies for the treatment of adenocarcinoma of the prostate necessitates an increased understanding of the cellular and molecular events involved in the generation of primary prostate cancer and its metastatic progression.

Four human prostate cancer cell lines (LNCaP, DU145, PC-3, TSU-Pr1), initiated from metastic lesions, have provided the basis for the majority of in vitro experiments concerning prostate cancer. Extensive progress has been made towards the in vitro cultivation of short-term lines from primary (nonmetastatic) prostate cancers. The advances have included culture media development and improvements in fresh tissue preparation and prostate epithelial cell culture techniques (3,4). However, the establishment and maintenance of long-term human prostate epithelial cell lines from primary tumors has been unsuccessful in the absence of in vitro immortalization. To this end, there exist only a small number of reports describing long-term immortalized cell lines, and these have been limited to normal prostatic epithelial cultures (5,6,7,8). Thus, the goal of the current study was to develop reliable methods for generating continuously proliferating prostate cancer cell lines derived from primary tumors.

Beyond the difficulties inherent in establishing immortal prostate epithelial cell lines are the problems associated with distinguishing cultivated prostate cancer from normal epithelial cells. Past cytogenetic evaluation of multiple short-term prostate epithelial cell cultures has revealed that the majority of lines generated from localized prostate cancers exhibit a normal male karyotype (9,10,11). This, combined with the unremarkable microscopic morphology of short-term cultures and a pervasive lack of success with xenotransplantation, has rendered accurate identification and characterization of human primary prostate cancer cell lines extremely difficult.

The initiation of prostate cancer is believed to occur as a result of multiple genetic changes within the cell, including the inactivation of potential tumor suppressor genes as manifested by allelic chromosomal deletions (reviewed in 12). Early studies examining chromosomal deletions in fresh (noncultured) primary prostate cancer speciments exhibited allelic loss of heterozygosity (LOH) on chromosomes 10q and 16q (13,14,15). Subsequent studies demonstrated a remarkably high percentage of allelic loss on the short arm of chromosome 8, thus moving chromosome 8p to the forefront of the list of potential sites for prostate cancer—associated tumor suppressor genes (16,17,18). Moreover, recent examination of 99 microdissected tumors (19) and 54 micro-dissected PIN lesions (20) for LOH on the short arm of chromosone 8p demonstrated strong evidence for the inactivation of a tumor suppressor gene(s) on chromosome 8p12–21 when compared to matched normal controls. Accordingly, examination of LOH within this minimal deletion region on chromosome 8p12–21 represents a potentially powerful alternative method for the identification and characterization of human prostate epithelial cell lines derived from primary tumors.

The present invention is the successful generation and unique genetic characterization of multiple immortalized human tumor cell lines derived from primary adenocarcinomas of the prostate.

SUMMARY OF THE INVENTION

The present invention provides for the isolation, immortalization, and characterization of long-term human epithelial cell lines derived from cancerous and normal prostate tissue and the potential applications of these cell lines in the research and therapy of prostate cancer. Specifically, the objects of the present invention are achieved using prostate epithelial cell lines with unlimited proliferation potential derived from both malignant and benign autologous specimens.

The cell lines of the present invention are useful as models in epithelial cell oncogenesis studies. For example, the immortalized epithelial prostate cell lines of the present invention are particularly useful for understanding the tumorigenesis of prostate cancer. The present invention provides for immortalized benign adult prostate cell lines for use in combination with immortalized, autologous malignant adult prostate cell lines as reagents for defining the genetic events leading from the benign to the malignant cellular phenotype, and for investigating the role of heredity in prostate cancer.

The present invention is an isolated, immortalized, malignant, human adult prostatic epithelial cell line. Another aspect of the invention is a cloned immortalized, malignant adult prostatic epithelial cell line characterized as having at least one allelic loss of heterozygosity (LOH). A further aspect of the invention is a cloned, immortalized, malignant, human adult prostatic epithelial cell line characterized as having loss of one or more alleles on chromosome 1, 8p, 10 and/or 16.

The cell lines of the present invention can be utilized in a method of producing a preselected protein and a method of producing proteins of epithelial cell origin. For example, the cell lines of the present invention are useful for the isolation of malignant prostate-associated proteins which could serve as markers for diagnosis or targets for immunotherapy. In one embodiment of the invention, a method for the production of proteins is provided comprising the steps of culturing the epithelial cell lines of the present invention and collecting one or more proteins produced by the novel cells. Identification of the genes encoding such proteins, using standard scientific practice, would enable construction of recombinant vectors for efficient large-scale production of the protein or portion thereof.

The cell lines of the present invention are also useful for testing the effects of therapeutic agents against prostate cancer in vitro, for example, chemotherapeutic drugs, biologic response modifiers, or genetic reagents such as antisense oligonucleotides.

The cell lines of the present invention are also useful as a whole cell vaccine for treating or preventing the recurrence of prostate cancer. The whole cell vaccine may be administered in the native form, in combination with adjuvants, or as modified by transgenes encoding, for example, various cytokines, chemokines, adhesion molecules, or MHC molecules.

The cell lines of the present invention are also therapeutically useful as stimulants for raising prostate cancer-reactive antibodies or immune cells from peripheral blood or lymph node cells for administration to prostate cancer patients.

The present invention also provides for immortal prostate cell lines for use in molecular cloning of malignant prostate-associated antigens recognized by the immune system. These antigens are then developed into recombinant vaccines directed to the prevention or cure of prostate cancer.

The present invention further provides for pharmaceutical compositions comprising one or more of the immortal cell lines of the present invention, and for pharmacological, therapeutic and diagnostic uses for the immortal cell lines and pharmacological compositions comprising the same.

These and other objects of the present invention will become apparent in light of the accompanying disclosure and annexed figures.

DETAILED DESCRIPTION OF THE INVENTION

Figure 1A:
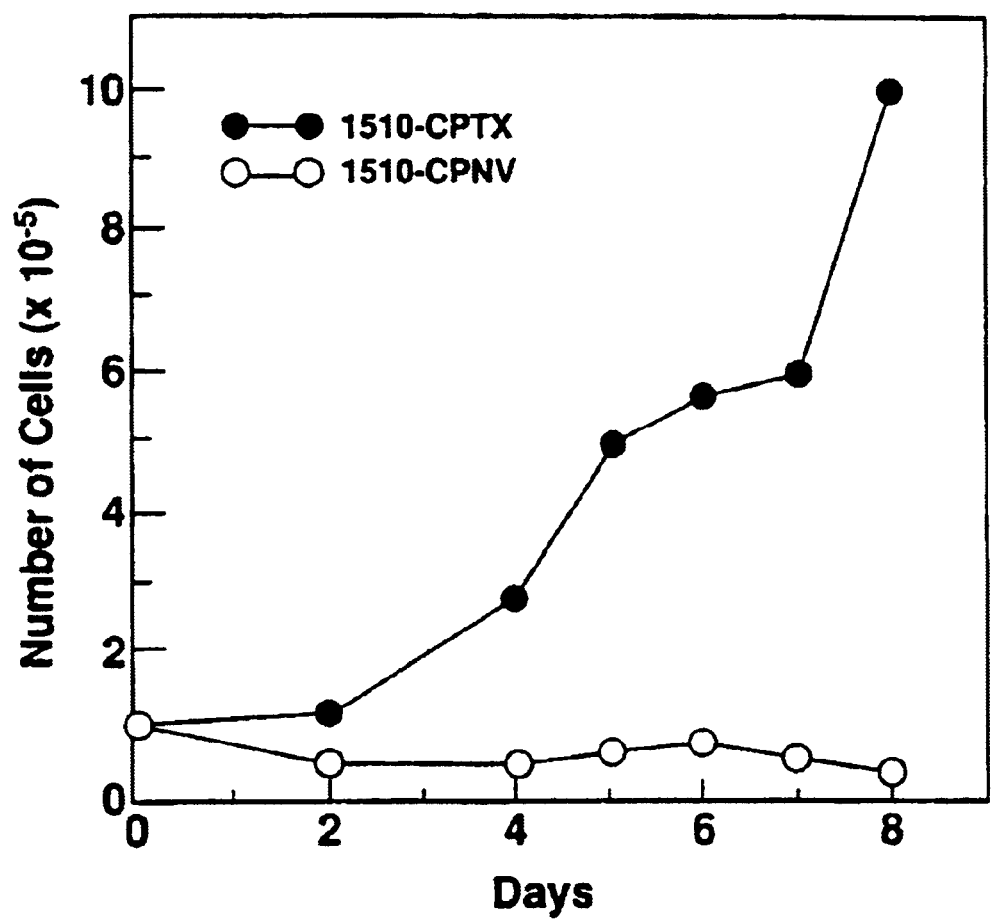
FIG. 1A and 1B. Morphologic and growth characteristics of an immortalized prostate epithelial cell line. (1A) Immortalization with the retrovirus LXSN16E6E7 was necessary to achieve continued proliferation of culture 1510-CP, initiated from a prostate cancer specimen. Cells were transduced (1510CPTX) or not (1510-CPNV) at culture passage 3, and proliferation in 24-well plates was monitored at passages 10 and 5, respectively. (1B) Photomicrograph of 1510-CPTX after 10 culture passages (200×, phase contrast). This culture appearance is typical of other prostate epithelial cell lines generated from benign or malignant specimens.

The present invention provides for the isolation, immortalization, and characterization of human adult prostate epithelial cell lines and clones derived from a number of fresh surgical specimens, including normal prostate and prostate cancer cell lines, and their potential applications in research and therapy.

The present invention generally provides immortal cell lines and clones of cell lines and pharmaceutical compositions comprising one or more of said cell lines, and their use as pharmaceutically active agents.

Specifically, the present invention provides cell lines of immortalized malignant adult prostate epithelial cell lines as well as matched autologous immortalized malignant and normal adult prostate epithelial cell lines. The immortalized prostate epithelial cell lines are herein designated as 1510-CP(carcinoma prostate), designated 1510-CPTX deposited on Aug. 22, 1999 with the ATCC, 10801 University Boulevard, Manassas, Va. 20110-2209 as PTA 604, 1512-NP(normal prostate), 1512-CP designated 1512-CPTX deposited on Aug. 22, 1999 with the ATCC, 10801 University Boulevard, Manassas, Va., 20110-2209 as PTA 606, 1519-CP, deposited as 1519-CPTX" deposited on Aug. 22, 1999 with the ATCC, 10801 University Boulevard, Manassas, Va., 20110-2209 as PTA 606 under the terms of the Budapest Treaty, 1532-NP (1532-NP, designated 1532-NPTX, has been deposited on Feb. 2, 1996 with the American Type Culture Collection (ATCC) in 10801 University Boulevard, Manassas Va., 20110-2209 under Accession No. CRL-12036), 1532-CP1, 1532-CP2 (1532-CP2, designated 1532-CP2TX, has been deposited on Feb. 2, 1996 with the ATCC in 10801 University Boulevard, Manassas, Va., 20110-2209 under Accession No. CRL-12038), 1535-NP (1535-NP, designed 1535-NPTX has been deposited on Feb. 2, 1996 in the ATCC in 10801 University Boulevard, Manassas, Va., 20110-2209 under Accession No. CRL-12039), 1535-SV(seminal vesicle), 1535-CP1 (1535-CP1, designated 1535-CP1TX, has been deposited on Feb. 2, 1996 with the ATCC in 10801 University Boulevard, Manassas, Va., 20110-2209 under Accession No. CRL-12041), 1535-CP2, 1542-NP (1542-NP, designated 1542-NPTX, has been deposited on Feb. 2, 1996 with the ATCC in 10801 University Boulevard, Manassas, Va., 20110-2209 under Accession No. CRL-12040), 1542-SV, 1542-CP1, 1542-CP2, and 1542-CP3 (1542-CP3, designated 1542-CP3TX, has been deposited on Feb. 2, 1996 with the ATCC in 10801 University Boulevard, Manassas, Va., 20110-2209 under Accession No. CRL-12037). All ATCC deposits were made under provisions of the Budapest Treaty.

The present invention also provides cloned, immortalized malignant prostate epithelial cell lines. Furthermore, the present invention also provides such clones characterized as having at least one allelic loss of heterozygosity (LOH).

In one embodiment, the cloned, immortalized, malignant, human, adult prostate epithelial cell line is characterized as having at least one allelic loss of heterozygosity. The loss of heterozygosity may occur on one or more chromosomes such as chromosome 1, 8, 10 and 16. In one embodiment, the cloned, immortalized, malignant, human, adult prostate epithelial cell line is characterized as having loss of heterozygosity at one or more loci on chromosome 8p. In a further embodiment, the cloned immortalized malignant prostate epithelial cell line has one or more allelic loss of heterozygosity at loci 12 through 21 on chromosome 8p.

In a particular embodiment, the cloned immortalized malignant, human, adult prostate epithelial cell line is characterized as having loss of the lower alleles of D8S133, D8S136 and D8S131. The cloned immortalized cell line has the identifying characteristics of a cloned immortalized malignant, human, adult prostate epithelial cell line 1542-$CP_3TX.8.1$ deposited as ATCC CRL-12265 on Jan. 15, 1997 with the American Type Culture Collection in 10801 University Boulevard, Manassas, Va., 20110-2209 under the terms of the Budapest Treaty.

In another particular embodiment, the cloned, immortalized, malignant, human, adult prostate epithelial cell line is characterized as having loss of the upper alleles of D8S133, D8S136, and D8S131. The cloned, immortalized cell line has the identifying characteristics of a cloned, immortalized, malignant, human, adult prostate epithelial cell line 1542-$CP_3TX.8.4$ deposited as ATCC CRL-12264 on Jan. 15, 1997 with the American Type Culture Collection in 10801 University Boulevard, Manassas, Va., 20110-2209 under the terms of the Budapest Treaty.

In another particular embodiment, the cloned, immortalized, malignant, human, adult prostate epithelial cell line is characterized as having loss of the lower alleles of SFTP-2, D8S136 and D8S131 and the upper alleles of D8S133 and NEFL. The cloned cell line has the identifying characteristics of a cloned malignant prostate epithelial cell line 1535-$CP_1TX.14.3$ deposited as ATCC CRL-12263 on Jan. 15, 1997 with the American Type Culture Collection in 10801 University Boulevard, Manassas, Va., 20110-2209 under the terms of the Budapest Treaty.

The cell lines and cloned cells of the present invention are immortalized using the human papillomavirus (HPV) gene or portion thereof. In one embodiment, the malignant cells are immortalized using the portion of HPV encoding E6 and E7 carried in a recombinant retrovirus. Cultures of the immortalized malignant prostate epithelial cells of the present invention remain stable and viable with continuous passage for over 1 year and longer.

The present invention also provides a method of isolating and cloning pure cell lines of human, adult prostate epithelial cells. Specifically, the method is effective in removing nonepithelial cells from the cultures, in particular in removing fibroblasts from the cultures. The method entails the careful dissection of fresh primary tumors into cells or tissues morphologically resembling the normal prostate gland and those resembling the malignant prostate. To prevent the growth of fibroblasts, cells are cultured in medium with little or no fetal bovine serum and/or cholera toxin. Differential trypsinization may also be used to eliminate fibroblasts from cultured prostate epithelial cells. The resulting epithelial cell lines are >90% pure, preferably 100% pure. Subsequent cloning of the cell lines results in cells which are 100% pure epithelial cells.

Another aspect of the present invention is a method of selecting for immortalized malignant prostate epithelial cells. The prior art has used markers such as PSA expression, PAP expression, PSA up-regulation by androgen, malignant growth in nude mice and aneuploid karyotypes as means of distinguishing malignant prostate epithelial cells from normal prostate epithelial cells. However, these markers do not consistently distinguish malignant prostate epithelial cells from normal cells. The present method of selecting for immortalized malignant prostate epithelial cells based on loss of heterozygosity provides a consistant, reproducible method of selection. The method employs at least one DNA marker that identifies a specific loss of allele on a particular chromosome. In one embodiment of the method, the DNA marker identifies a specific loss of allele on chromosome 8p. The method may use multiple DNA markers to identify more than one loss of allele on a particular chromosome, or allelic loss on multiple chromosomes.

In the method of detecting and identifying malignant cells, PCR primers specific for distinct chromosomal loci are incubated with DNA isolated from an immortalized prostate epithelial cell line, and a PCR assay is conducted.

The amplified products are analysed for LOH at one or more loci in comparison with a DNA control taken from known normal cells. One criterion for designating LOH is at least 75% loss of one allele by the malignant cell as compared to the normal DNA control, determined by visual inspection of autoradiographs. Other methods known to those practiced in the art, include densitometry analysis to detect differences, the criteria for designating LOH being at least 30% loss of one allele by the malignant cell.

The immortalized, malignant, prostate epithelial cell lines and clones of the present invention are useful in identifying novel genes unique to or overexpressed in malignant prostatic epithelial cells and which are not found or are not active in normal prostatic epithelial cells. The novel genes include but are not limited to transforming genes, growth factor genes, oncogenes, tumor suppressor genes. These genes may be identified using methods of RNA subtraction analysis known to those practiced in the art, such as standard subtractive hybridization, differential display, or representative differential anaylsis (RDA) (51, 52). The novel genes are cloned using standard molecular biology techniques as are known in the art. Identification of novel genes associated with the development of prostate cancer allows for the development of antisense oligonucleotides useful in inhibiting or preventing prostate cancer (42) and for the development of recombinant DNA vaccines.

The cell lines of the present invention are useful as models in epithelial cell oncogenesis studies. For example, the epithelial prostate cell lines of the present invention are particularly useful for understanding the tumorigenesis of prostate cancer. The present invention provides for a benign prostate cell line for use in combination with a malignant prostate cell line derived from the same patient as reagents for defining the genetic events leading from the benign to the malignant cellular phenotype, and for investigating the role of heredity in prostate cancer.

The cell lines of the present invention can be utilized in a method of producing a preselected protein or portion thereof and a method of producing proteins of malignant, prostatic, epithelial cell origin. For example, the cell lines of the present invention are useful for the isolation of prostate cancer associated proteins which could serve as markers for diagnosis or targets for immunotherapy. In one embodiment of the invention, a method for the production of protein is provided comprising the steps of culturing the epithelial cell lines of the present invention and collecting one or more proteins produced by the novel cells. Identification of the genes encoding such protein, using standard scientific practice, enables construction of recombinant vectors and host cells for efficient large-scale production of the protein or portions thereof.

The present invention encompasses a novel recombinant virus expressing a prostate cancer-associate protein, or portion thereof. The recombinant virus may also express one or more costimulatory molecules, cytokines, MHC molecules, chemokines and the like for enhancing the immune response to the prostate cancer-associate protein or portion thereof. Method for constructing and expressing exogenous gene products from recombinant virus vectors are known in the art (43–50).

The present invention encompasses isolated DNA or RNA derived from immortalized human adult prostate epithelial cell lines or clones. Of interest is DNA or RNA isolated from immortalized human malignant adult prostate epithelial cells exhibiting LOH. Also of interest is DNA and RNA derived from matched autologous immortalized human normal and malignant adult prostate epithelial cells. The isolated DNA, RNA or oligonucleotides thereof may be used in the detection and diagnosis of prostate cancer or precancer in an individual. The DNA, RNA or oligonucleotides may be used as probes and/or primers in standard molecular biology methods such as Southern blot analysis, Northern blot anaylsis, PCR, RT-PCR and the like for detection and diagnosis of prostate cancer or precancer. Of interest is DNA, and the corresponding RNA, having loss of alleles on one or more chromosomes such as 1, 8, 10 and 16. Of particular interest is DNA, and the corresponding RNA, having loss of one or more alleles on chromosome 8.

Naked DNA encoding prostate cancer antigen or epitopes thereof may be used for active immunotherapy against prostate cancer. Techniques known in the art may be used to inject the naked DNA or naked DNA linked to lipids into muscle or skin to elicite both a cellular and humoral immune response to the encoded prostate cancer antigen or epitopes thereof (33–41).

The cell lines of the present invention are also useful for testing the effects of therapeutic agents against prostate cancer in vivo or in vitro. For example, chemotherapeutic drugs, biologic response modifiers, or genetic reagents such as anti-sense oligonucleotides may be screened for efficacy. The chemical or agent to be tested is placed in the presence of the cells in vivo or in vitro. After a suitable period of exposure, the effect of the chemical or agent on the cell is assessed by methods known in the art such as cytotoxicity assay, protein inhibition assays, inhibition of tumor growth and the like. A chemical or agent that inhibits a vital metabolic function or kills the cells is considered an effective therapeutic agent.

The cell lines and clones of the present invention are also useful as a whole cell vaccine for treating or preventing the recurrence of prostate cancer. The whole cell vaccine may be administered in the native form, in combination with adjuvants, or as modified by transgenes encoding, for example, various cytokines, chemokines, costimulatory molecules, adhesion molecules, MHC molecules and the like. Such modifications may be used to enhance the immunotherapeutic effect of the immunogen and vaccine of the present invention.

The genes may be incorporated into the immortalized human malignant prostatic epithelial cell lines and clones by methods known in the art such as electroporation, polybrene-induced DNA tranfection, via plasmids, via recombinant virus, and the like. Recombinant virus containing one or more genes of interest may be constructed as described in WO94/16716, WO96/11279 and WO96/10419.

Costimulatory molecules which may be employed in the present invention include but are not limited to B7-1, B7-2, B7-3, ICAM-1, LFA-1, LFA-3, CD72 and the like.

Cytokines which may be utilized in the present invention include but are not limited to IL-2, GM-CSF, TNFα, IFNγ, IL-12, IL-4, IL-7, and the like.

MHC molecules include but are not limited to class I or class II molecules and the like. Nonclassical MHC molecules or MHC-like molecules such as CD1 may also be used.

Chemokines include but are not limited to RANTES, IL-8, MIP1-alpha, MIP1-beta, and the like.

The cell lines of the present invention are also therapeutically useful as stimulants for raising prostate cancer-reactive antibodies or immune cells from peripheral blood or lymph node cells for administration to prostate cancer patients.

The present invention also provides for immortal prostate cell lines for use in molecular cloning of prostate cancer-associated antigens recognized by the immune system. These antigens are then developed into recombinant vaccines directed to the prevention or cure of prostate cancer.

The present invention further provides for pharmaceutical compositions comprising the immortal cell lines of the present invention, and for pharmacological, therapeutic and diagnostic uses for the immortal cell lines and pharmacological compositions comprising the same.

Pharmaceutical compositions, vaccines and immunogens can be prepared in accordance with standard techniques known to those skilled in the pharmaceutical art. Such compositions can be administered to a patient in need of such administration in dosages and by techniques known to those skilled in the art taking into consideration such factors as the age, weight and condition of the particular patient, and the route of administration.

The immunization protocol for the compositions, vaccines and immunogens may be via a parenteral route (intravenous, intraperitoneal, intradermal, intramuscular or subcutaneous). The composition, vaccine and immunogen may be administered directly into a tumor mass. Moreover, the compositions may be used in vitro to stimulate antigen specific cytotoxic T lymphocytes which are then administered back to the patient.

The compositions, vaccines and immunogens may be coadministered or sequentially administered with adjuvants, such as alum, incomplete Freund's adjuvant and the like, cytokines, costimulatory molecules, chemokines, adhesion molecules, MHC molecules and the like. Additionally, the compositions, vaccines and immunogens may be coadministered or sequentially administered with anti-neoplastic, antitumor, anticancer agents and/or with agents which reduce or alleviate ill effects of antineoplastic, antitumor or anticancer agents.

Examples of vaccines or compositions of the invention include liquid preparations such as suspension, syrups, elixirs and preparations for parenteral, subcutaneous, intradermal, intramuscular or intravenous administration. The pharmaceutical compositions may be in admixture with a suitable carrier, diluent or excipient such as sterile water, physiologicol saline, glucose and the like.

The efficacy of the treatment can be assessed by production of antibody or immune cells that recognize the malignant cell or prostate cancer peptide or portion thereof, assessment of antigen specific cytotoxicity, specific cytokine production or tumor regression.

The immortalized, human adult prostate epithelial cells or portions thereof may be provided in the form of a kit. The kit may include one or more immortalized, human, adult prostate epithelial cells or portions thereof. Portions encompass lysed cells, cell fragments, intracellular contents, extracellular components, protein, DNA, RNA, glycolipids and the like. Kits may also include autologous immortalized, human adult malignant prostate epithelial cells or portions thereof in combination with autologous immortalized, human adult normal prostate epithelial cells or portions thereof. In one embodiment, the kit comprises the immortalized, human adult normal epithelial cell line, 1532-NP in combination with the autologous, immortalized, human, adult, malignant cell line 1532-CP1 and/or 1532-CP2. In another embodiment, the kit comprises the immortalized, human, adult, normal epithelial cell line, 1535-NP in combination with the autologous immortalized human, adult, malignant cell line 1535-CP1, 1535-CP2 and/or 1535-CP1TX.14.3. In yet another embodiment the kit comprises the immortalized, human, adult normal epithelial cell line, 1542-NP in combination with one or more of the autologous immortalized human, adult malignant cell lines 1542-CP1, 1542-CP2, 1542-CP3, 1542-CP$_3$TX.8.1 and 1542-CP$_3$TX.8.4. The kit may include a separate container containing a suitable carrier, diluent or excipient. The kit may also include an adjuvant, cytokine, costimulatory molecule, chemokine, adhesion molecule, MHC molecule, antineoplastic agent, antitumor agent, immunoassay reagents, PCR reagents, radiolabels and the like. Additionally, the kit may include instructions for mixing or combining ingredients and/or administration.

The term "immortalized" as used herein means that the cell line grows continually without senescence when cultured in vitro in a suitable growth medium.

The present invention also encompasses polyclonal and monoclonal antibodies directed to the cell lines of this invention. These antibodies can then be used to prepare antibody containing compositions used in the methods of the present invention. The antibodies are prepared via techniques well known to those having ordinary skill in the art. In particular, monoclonal antibodies produced against the immortal prostate cell lines of the present invention are useful in the detection and therapy of prostate cancer. The antibody or antigen binding portion thereof binds to malignant prostate cells. The antibody or antigen binding portion thereof is immunoreactive with at least one prostate tumor rejection antigen or with at least one prostate cancer-associated antigens and epitopes thereof.

Exemplary antibody molecules are intact immunoglobulin molecules, substantially intact immunoglobulin molecules or those portions of an immunoglobulin molecule that contain the antigen binding site, including F(ab), F(ab)2, and F(v). Polyclonal or monoclonal antibodies may be produced by methods known in the art. (Kohler and Milstein, 1975 *Nature* 256:495–497; Campbell "Monoclonal Antibody Technology, the Production and Characterization of Rodent and Human Hybridomas" in Burdon et al (eds) (1985), "Laboratory Techniques in Biochemistry and Molecular Biology", Vol. 13, Elsevier Science Publishers, Amsterdam). The antibodies or portions thereof may also be produced by genetic engineering including chimeric antibody, single chain antibody as described in Traunecker et al *The EMBO J.* 10 (2):3655–3659, 1991 and Milenic, D. E. et al *Cancer Research* 51, 6363–6371, 1991 and humanized antibody as described in U.S. Pat. No. 5,530,101.

The antibody or portion thereof may be used as an immunotherapeutic. The antibody or portion thereof may be administered alone, or in combination with chemotherapeutics or immunosuppressive agents as are known in the art.

The antibody or portion thereof may also be used as an immunotoxin to specifically target and kill malignant prostatic cells. Immunotoxins are characterized by two components and are particularly useful for killing selected cells in vitro or in vivo. One component is a cytotoxic agent which is usually fatal to a cell when attached or absorbed, The second component, known as the delivery vehicle, provides a means for delivering the toxic agent to a particular cell type, such as malignant prostate cells. The two components are commonly bonded together by any of a variety of well-known chemical procedures. For example, when the cytotoxic agent is a protein, the linkage to the antibody may be by way of hetero-bifunctional crosslinkers, e.g., SPDP, carbodiimide, glutaraldehyde, and the like. Production of various immunotoxins is well-known in the art, for example in "Monoclonal Antibody-Toxin Conjugates: Aiming the Magic Bullet", Thorpe et al, Monoclonal Antibodies in Clinical Medicine, *Academic Press, pp.* 168–190 (1982). The components may also be linked genetically as described in Chaudhary et al *Nature* 339, 394 (1989).

A variety of cytotoxic agents are suitable for use in immunotoxins. Cytotoxic agents include but are not limited to radionuclides, such as Iodine-131 or other isotopes of iodine, Yttrium-90, Rhenium-188, and Bismuth-212 or other alpha emitters; a number of chemotherapeutic drugs, such as vindesine, methotrexate, adriamycin, taxol, and cisplatinum; and cytotoxic proteins such as ribosomal inhibiting proteins like pokeweed antiviral protein, Pseudomonas exotoxin A, ricin, diphtheria toxin, ricin A chain and the like (see "Chimeric Toxins", Olsnes and Phil, *Pharmac. Ther.* 25, 355–381 (1982), and "Monoclonal Antibodies for Cancer Detection and Therapy", eds. Baldwin and Byers, pp. 159–179, 224–266, Academic Press, 1985).

For diagnostic purposes, the antibody may be either labeled or unlabeled. Unlabeled antibody may be used in combination with other labeled antibodies. A wide variety of labels may be employed, such as radionculides, fluors, enzymes, enzyme substrates, enzyme cofactors, enzyme inhibitors, ligands and the like. Numerous types of immunoassays are available and are well-known to those skilled in the art.

The cell lines, genes, proteins, and antibodies of the present invention are useful in a variety of therapeutic and diagnostic settings. These are described with more specificity below.

The references disclosed are incorporated herein by reference.

EXAMPLE I (1) Characteristics of Patients from whom Cultured Epithelial Cell Lines were Initiated.

Prostate epithelial cell lines were initiated from radical prostatectomy specimens from 6 consecutive patients with intermediate to high grade tumors (Gleason grades 6–8). (See Table 1). Cell cultures were initiated by mechanical disruption or enzymatic digestion of primary tumor nodules excised from fresh radical prostatectomy specimens. See Example II for detailed description of culture methods.

TABLE 1

Prostate Cancer Patients: Clinical Information

| Patient # | Age(yrs) | Pre-Op PSA (ng/ml) | Post-Op Gleason Grade |
|---|---|---|---|
| 1510 | 51 | 14.9 | 3 + 3 = 6 |
| 1512 | 64 | 14.0 | 4 + 3 = 7 |
| 1519 | 54 | 7.7 | 4 + 4 = 8 |
| 1532 | 52 | 5.0 | 3 + 3 = 6 |
| 1535 | 66 | 2.2 | 3 + 5 = 8 |
| 1542 | 48 | 14.3 | 3 + 5 = 8 |

(2) Pathological Analysis of Tissue Specimens.

Pathological analysis of fresh tissue specimens used to initiate prostate cancer cell lines revealed that some cancer specimens were pure tumor, while others consisted of mixtures of benign and malignant cells. See Table 2: Preliminary identification of specimens was assigned on gross examination by an experienced pathologist. Microscopic identification was assigned on examination of 10 high power fields by an experienced pathologist. BPH=benign prostatic hypertrophy. PIN=prostatic intraepithelial neoplasia. $^a$=a mixture of cell types. $^b$=80% of specimen consisted of benign fibromuscular stroma. $^c$=one microscopic focus of cancer noted.

TABLE 2

Pathologic Analysis of Fresh Prostate Specimens

| Patient # | Gross Specimen | Microscopic Analysis (estimate % total cells) | | | |
|---|---|---|---|---|---|
| | | Benign | BPH | PIN | Tumor |
| 1510 | Tumor | 40$^a$ | 0 | 40$^a$ | 60 |
| 1512 | Normal Prostate | 100 | 0 | 0 | 0 |
| | Tumor | 90$^a$ | 90$^a$ | 0 | 10 |
| 1519 | Normal Prostate | 100 | 0 | 0 | 0 |
| | Tumor | 50 | 0 | 0 | 50 |
| 1532 | Normal Prostate | 95 | 0 | 5 | 0 |
| | Tumor 1 | 100 | 0 | 0 | 0 |
| | Tumor 2 | 0 | 0 | 0 | 100 |
| 1535 | Normal Prostate | 20$^b$ | 0 | 0 | 0 |
| | Seminal Vesicle | 100 | 0 | 0 | 0 |
| | Tumor 1 | 0 | 0 | 0 | 100 |
| | Tumor 2 | 5 | 0 | 10 | 85 |
| 1542 | Normal Prostate | 0 | 95 | 5 | —$^c$ |
| | Seminal Vesicle | 100 | 0 | 0 | 0 |
| | Tumor 1 | 0 | 0 | 40 | 60 |
| | Tumor 2 | 0 | 0 | 40 | 60 |
| | Tumor 3 | 0 | 0 | 40 | 60 |

(3) Confirmation of Epithelial Origin of Prostate-derived Cell Lines.

The epithelial origin of prostate-derived cell lines was confirmed with cytokeratin staining. Both high and low molecular weight cytokeratins were expressed by all 16 cell lines generated from 6 radical prostatectomy specimens (normal prostate, prostate cancer, normal seminal vesicle). With the exception of an early passage of 1519-CP, none of the prostate-derived cell lines expressed PSA or PAP. See Table 3: F=fibroblasts, NP=normal prostate, SV=seminal vesicle, CP=carcinoma prostate. $^1$=includes both high and low molecular weight keratins. $^b$=PSA and PAP expression was noted at culture passage number 5 but was lost after continued passage in vitro. $^c$=observed staining was noted as possible background.

TABLE 3

Immunocytochemical Analysis of Immortalized Prostate Epithelial Cell Lines

| Patient # | Cell Source | % Positive Cells (stain intensity) | | |
|---|---|---|---|---|
| | | PSA | PAP | Cytokeratin$^a$ |
| 1510 | F | 0 | 0 | 25(1–2 +)$^c$ |
| | CP | 0 | 0 | >75(4+) |
| 1512 | NP | 0 | 0 | >75(4+) |
| | CP | 0 | 0 | >75(4+) |
| 1519 | F | 0 | 0 | >75(1+)$^c$ |
| | CP | >75(2–3+)$^b$ | >75(4+)$^b$ | >75(4+) |
| 1532 | F | 0 | 0 | 5(1–2+) |
| | NP | 0 | 0 | >75(4+) |
| | CP1 | 0 | 0 | >75(4+) |
| | CP2 | 0 | 0 | >75(4+) |
| 1535 | NP | 0 | 0 | >75(4+) |
| | SV | 0 | 0 | >75(4+) |
| | CP1 | 0 | 0 | >75(4+) |
| | CP2 | 0 | 0 | >75(4+) |
| 1542 | NP | 0 | 0 | >75(4+) |
| | SV | 0 | 0 | >75(4+) |
| | CP1 | 0 | 0 | >75(4+) |
| | CP2 | 0 | 0 | >75(4+) |
| | CP3 | 0 | 0 | >75(4+) |
| LNCaP | | >75(4+) | 25(3–4+) | >75(4+) |

(4) Cell Surface Phenotyping.

Cell surface phenotyping is described in Example II, Table 6.

(5) Genetic Analysis of Prostate Epithelial Cell Lines.

Allelic loss on chromosome 8 has been associated with PIN and invasive prostate cancer, and thus represents an alternative method for characterizing epithelial cell lines derived from prostate cancer specimens. Examination of allelic loss at 10 separate loci on chromosome 8p using PCR (polymerase chain reaction) revealed loss of heterozygosity (LOH) at one locus in 1 of 9 uncloned cancer-derived cell lines examined, suggesting that this is an established long-term primary prostate tumor cell line. Although extreme care was taken to dissect the purest tumor fragments possible for in vitro cultivation, subsequent microscopic evaluation of the original tumor specimens exhibited a variable mixture of benign epithelium, BPH, PIN, and/or invasive tumor (see Table 2) which could mask LOH, making epithelial cell cloning necessary for precise characterization. Definitive genetic characterization of the prostate epithelial cell cultures described herein, and single cell cloning of said lines, are described below.

EXAMPLE II

Single Cell Cloning and Characterization of Immortalized Malignant Prostatic Epithelial Cells Materials and Methods Initiation of Primary Cell Cultures. Tissue specimens used for generating cell lines were obtained from six consecutive patients under going radical prostatectomies at the NCI for treatment of intermediate to high grade localized prostate cancer (Gleason grades 6–8, tumor stages T2C to T3C). Fresh prostatectomy specimens obtained directly from the operating room were dissected under sterile conditions by an experienced pathologist. Tissues designated as normal prostate, prostate cancer, or normal seminal vesicle on gross inspection were dissected separately for the purpose of generating cell cultures. Cultures were initiated by mechanical disruption (<1 cm diameter fragments) or enzymatic digestion (>1 cm fragments) (21). Specimens from patients 1510 and 1512 were prepared by enzymatic digestion, while subsequent cultures were initiated by mechanical disruption. For enzymatic digestion, minced tissue was suspended in 100 ml of digestion media and left on a stir plate overnight at room temperature. The resulting single cell suspension was then washed with sterile PBS, resuspended in growth medium (see below) and dispensed into 6-well plates coated with type I rat tail collagen (Collaborative Biomedical Products, Bedford, Mass.). For mechanical disruption of specimens, tissue fragments were carefully minced into 2–3 mm cubes in a small volume of growth medium, and the resultant slurry of tissue and cells was dispensed into 6-well plates. All cultures were initiated in a volume of 1 ml per well and incubated at 37° C., 5% $CO_2$. They were not disturbed for 2–3 days to allow viable cells and tissue chucks to settle and attach to the plates. Then, the unattached debris was carefully aspirated, and wells were refed with 3–5 ml fresh medium. Culture medium was routinely replaced every 2–4 days and proliferating adherent cells were passaged following detachment with trypsin. Established growing cultures were maintained in tissue culture flasks (Falcon, Becton Dickinson, Lincoln Park, N.J.). Growth medium for prostate and seminal vesicle epithelial cell-lines consisted of keratinocyte serum free medium (Keratinocyte-SFM. GIBCO-BRL, Grand Island, N.Y.) containing 25 μg/ml bovine pituitary extract, 5 ng/ml epidermal growth factor, 2 mM L-glutamine, 10 mM HEPES buffer, antibiotics and 5% heat-inactivated fetal bovine serum (FBS) (Biofluids, Rockville, Md.). For the initiation of epithelial cultures from fresh tissue specimens, the concentration of FBS was reduced to 1–2% and/or cholera toxin (Sigma, St. Louis, Mo.) was added at 10–20 ng/ml to guard against outgrowth of contaminating fibroblasts. In the rare event that fibroblasts persisted in epithelial cell cultures, differential trypsinization (incubation for 1–2 min at 37° C., followed by washing away detached fibroblasts to leave the more adherent epithelial cells) was extremely successful in achieving pure epithelial cell cultures.

Autologous fibroblast cell lines were generated from mechanically disrupted benign prostate stromal tissue and cultured in RPMI 1640 medium containing 10% heat-inactivated FBS. Autologous Epstein-Barr virus-transformed B cell lines were generated using standard techniques and cultured in RPMI 1640 +10% FBS.

Metastatic Prostate Cancer Cell Cultures. The adherent cell lines LNCaP, DU145, PC-3 (ATCC, CRL1740, HTB 81, CRL1435, respectively) and TSU-Pr1 (kindly provided by Dr. William Isaacs, Johns Hopkins University, Baltimore, Md.; as described in Iizumi et al, *J. Urol.* 137:1304–1306, 1987) were maintained in RPMI 1640 medium supplemented with 10% FBS.

Immortalization of Primary Cell Cultures. Cell culture immortalization was accomplished by transduction of actively proliferating cells with a recombinant retrovirus encoding the E6 and E7 transforming proteins of human papillomavirus serotype 16 (HPV16) and the eukaryotic selection marker neomycin phosphotransferase, designated LXSN16E6E7 (generously provided by Dr. Denise Galloway, Fred Hutchinson Cancer Research Center, Seattle, Wash.) (22). In preparation for immortalization, short-term epithelial cell cultures (culture passage 1–3) were split 1:2 and allowed to reattach in 6-well plates for at least 48 h, yielding cultures which were 50–60% confluent. Transduction with the LXSN16E6E7 retrovirus was accomplished by replacing the culture medium with culture supernatant collected from the retrovirus producer line PA317 (22), in the presence of 10 μg/ml DEAE-dextran (Sigma), for a period of 24 h.

Single Cell Cloning of Immortalized Cell Cultures. Clonal populations of immortal epithelial cell cultures were generated for use in LOH characterization studies. Briefly, confluent cell cultures were harvested with trypsin, washed and counted. Cells were serially diluted to a concentration of 2–5 cells /ml in keratinocyte growth medium (see above) and dispensed into 8–10 individual 96 well flat bottom microculture plates at 200 μl/well ($\leq$1 cell/well). Confluent wells originating from dilutions of<1 cell/well were expanded to 24 well plates to ensure enough cells for DNA extraction and cryopreservation Immunocytochemical Analysis. For immunocytochemical studies of immortalized cultured cells, cells were harvested with trypsin, washed and pelleted. Cell pellets were subsequently fixed in 10% buffered formalin and embedded in paraffin. Fresh tissue sections from prostate specimens were also fixed in formalin and paraffin-embedded. Five micron sections were prepared from fresh tumor specimens and cultured cell blocks and mounted on charged slides (Fisher Scientific, Pittsburgh, Pa.) (23). Immunocytochemistry was performed using the avidin-biotin peroxidase complex method and the following primary antibodies: monoclonal anti-human prostate specific antigen (PSA) (Dako Corp, Carpenteria, Calif.); polyconal anti-human prostatic acid phosphatase (PAP) (Dako Corp, Carpenteria, Calif.); anti-human cytokeratin CAM 5.2 (Becton-Dickinson, San Jose, Calif.); and anti-human cytokeratin AE1/AE3 (Boehringer-Mannheim, Indianapolis, Ind.). Cell lines and tumor tissue sections were evaluated based on the percentage of cells staining (<25%, 25–50%, 50–75% or >75%) as well as staining intensity (1+ to 4+).

Flow Cytometry. For future studies and further characterization, it was of interest to determine the extent of expression of surface molecules of immunologic importance on the long-term prostate epithelial cell lines. Immortalized cell cultures were harvested and stained with the following monoclonal antibodies: CD54 (anti-ICAM-1), CD80(anti-B7.1), CD86 (anti-B7.2) (Becton-Dickinson), W6/32 (anti-HLA-A,B,C) and L243 (anti-HLA-DR) (ATCC, RockviUe, Md.) (21). To enhance surface expression of MHC molecules, cells were cultured in the presence of IFN-γ500 U/ml for 72 h prior to flow cytometric analysis.

Microdissection and DNA Extraction. Microdissection of selected foci of normal prostate epithelial cells or invasive tumor cells from formalin-fixed, paraffin-embedded tissue samples was performed under direct light microscopic visualization as described previously (24,25,26). Briefly, unstained formalin-fixed, paraffin-embedded 5 micron histologic tissue sections were prepared on glass slides and deparafrinized twice with xylene, rinsed twice with 95% ethanol, stained with eosin and air-dried. The adjacent section was stained with hematoxylin and eosin. Specific cells of interest were selected from the eosin stained slides and microdissected using a disposable, modified 30 gauge needle. DNA was extracted from $1–5\times10^3$ cells procured by microdissection. In some cases, cells from more than one dissected adjacent tubule of cancer or normal epithelium were combined. DNA was also extracted from 1–5×10⁴ cells obtained from actively growing immortalized cultures. Cells were immediately resuspended in a solution (20 µl for microdissected or 200 µl for cultured cells) containing 0.01 M TRIS-HCl pH8.0, 1 mM EDTA, 1% Tween 20, and 0.1 mg/ml proteinase K, and incubated overnight at 37° C. Following incubation, the mixture was boiled for 5–10 min to inactivate the proteinase K and stored at 4° C. for subsequent polymerase chain reaction (PCR) analysis.

Detection or Loss of Heterozygosity. The polymorphic DNA markers studied for the detection of LOH on chromosome 8p12–21 included: SFTP-2, D8S133, D8S136, NEFL, D8S137, D8S131, D8S339 and ANK. The PCR primer pairs used to amplify the DNA microsatellite markers is as follows:

1)SFTP2
Nucleic Acid Sequences: L16861

| Primers: | |
|---|---|
| Primer Name | Primer Sequence |
| SFTP2CA | CAGCCCAGACAGGCTGGAA (Seq. ID No. 1) |
| SFTP2GT | ACTTTTCTGGCCAAACTCCTG (Seq. ID No. 2) |

Amplified Seq Min Length: 0.111
Amplified Seq Max Length: 0.157
as described in Wood, S *Genomics* 24:597–600, 1994. SFTP2 maps in the region between 8p11–8p22.

2)D8S133
Nucleic Acid Sequences: M73471

| Primers: | |
|---|---|
| Primer Name | Primer Sequence |
| D8S133CA | CAGGTGGGAAAACTGAGGGA (Seq. ID No. 3) |
| D8S133GT | AGCAACTGTCAACATATTGCTC (Seq. ID No. 4) |

Amplified Seq Min Length: 0.094
Amplified Seq Max Length: 0.112
as described in Wood, S. *Cytogenet Cell Genet* 58:1932, 1991; Wood, S. *Genomics* 13:232, 1992.

3)D8S136

| Primers: | |
|---|---|
| Primer Name | Primer Sequence |
| D8S136CA | GCCCAAAGAGGAGAATAAA (Seq. ID No. 5) |
| D8S136GT | CTGTTTCCACACCGAAGC (Seq. ID No. 6) |

Amplified Seq Min Length: 0.071
Amplified Seq Max Length: 0.089
as described in Wood, S. *Cytogenet Cell Genet* 58:1932, 1991.

4)NEFL
Nucleic Acid Sequences: L04147

| Primers: | |
|---|---|
| Primer Name | Primer Sequence |
| 214 | GCAGTAGTGCCGCAGTTTCA (Seq. ID No. 7) |
| 215 | TGCAATTCATCTTCCTTTCT (Seq. ID No. 8) |

Amplified Seq Min Length: 0.137
Amplified Seq Max Length: 0.147
as described in Rogaev, E. *Hum, Mol. Genet.* 1:781, 1992.

5)D8S137
Nucleic Acid Sequences: X61694

| Primers: | |
|---|---|
| Primer Name | Primer Sequence |
| D8S137CA | AAATACCGAGACTCACACTATA (Seq. ID No. 9) |
| D8S137GT | GCTAATCAGGGAATCACCCAA (Seq. ID No. 10) |

Amplified Seq Min Length: 0.152
Amplified Seq Max Length: 0.161
as described in Wood, S. *Cytogenet Cell Genet* 58:1932, 1991; Wood, S. *Nucleic Acids Res.* 19:6664, 1991.

6)D8S131

| Primers: | |
|---|---|
| Primer Name | Primer Sequence |
| 131CA2-1 | ACATAGGCTGGAGAGTCACAGG (Seq. ID No. 11) |
| 131CA2-2 | GGATGAGGCTCAGCACACAAGC (Seq. ID No. 12) |

Amplified Seq Min Length: 0.132
Amplified Seq Max Length: 0.144
as described in citations: Yu, C E *Hum. Mol. Genet.* 3:211, 1994.

7)D8S339

| Primers: | |
|---|---|
| Primer Name | Primer Sequence |
| WT251-A | TAGATGTTACCATTTCAC (Seq. ID No. 13) |
| WT251-B | GATTAGATCTTGGATCAG (Seq. ID No. 14) |

Amplified Seq Min Length: 0.162
Amplified Seq Max Length: 0.176
as described in citations: Thomas, W. *Hum. Mol. Genet.* 2:828, 1993.

8)Ank
Nucleic Acid Sequences: D16990

| Primers: | |
|---|---|
| Primer Name | Primer Sequence |
| ANK1.PCR1.1 | TCCCAGATCGCTCTACATGA (Seq. ID No. 15) |
| ANK1.PCR1.2 | CACAGCTTCAGAAGTCACAG (Seq. ID No. 16) | as described in Polymeropoulos et al *Nucleic Acids Res* 19:969, 1991.

PCR was performed as previously described (19). Briefly, 12.5ul PCR reaction mixtures contained 200 $\mu$M dATP, dGTP and dTTP; 40 $\mu$M dCTP; 0.8 mM primers (Research Genetics, Huntsville, Ala., or synthesized on an Applied Biosystems DNA synthesizer); 2 $\mu$Ci [$\alpha$-$^{32}$P] dCTP; 16 $\mu$M tetramethylammonium chloride (27); 1× PCR reaction buffer (containing 1.25 mM MgCl$_2$) and 1 unit of Taq polymerase (Boehringer Mannheim). Five percent DMSO was added to reactions for markers D8S133 and D8S137 to improve amplification and resolution of the products. Reactions with all markers were performed as follows: 2 min at 95° C., followed by 28 to 40 cycles (depending on the marker) of annealing and extension (95° C. for 30 sec, annealing temp. for 30 sec, and 72° C. for 30 sec) and a 2 min incubation at 72° C. Annealing temperatures for each marker were determined empirically after an initial estimate based on primer length and composition.

The labeled amplified DNA samples were denatured for 5–10 min at 90° C. and loaded onto a gel consisting of 7% acrylamide (30:0.8 acrylamide: bisacrylamide), 5.6 M urea, 32% formamide and 1× TBE (0.089 M Tris pH 8.3, 0.089 M borate, 0.002 M EDTA) (28). Samples were electrophoresed at 95 for 2–4 h. Gels were then transferred to sequencing gel filter paper (Bio-Rad), and autoradiography was performed with Kodak X-OMAT film. The criterion for LOH was at least 75% loss of one allele compared with an autologous fresh PBL control, as determined by direct visualization by three independent investigators. When sufficient DNA was available, LOH was verified with at least two independent experiments.

Results

Tissue Procurement for Cell Culture. Being aware of the historical difficulties associated with generating immortal prostate cancer cell lines from primary (nonmetastatic) specimens, the largest grossly apparent tumor nodules (1–3 cm diameter) were initially selected as the fresh tissue source for generating cultures. Subsequent microscopic analysis of the neighboring tissue sections from the first three attempts (patients 1510, 1512, and 1519) revealed that "tumor" specimens actually contained a variable mixture of benign prostatic epithelium, benign prostatic hypertrophy (BPH), prostatic intraepithelial neoplasia (PIN) and invasive tumor cells. However, "normal" specimens from patients 1512 and 1519 consisted entirely of benign prostatic epithelium (Table 2).

To increase the likelihood of obtaining pure tumor tissue for starting tumor cell lines from subsequent patients, smaller tissue fragments (<1 cm) were procured with neighboring sections designated for tissue culture, frozen and paraffin sections. In addition, whenever possible, multiple distinct tumor tissue fragments were selected from individual specimens for culture initiation. By employing these more stringent conditions it was possible to obtain tissue sections containing at least 95% neoplastic cells (PIN plus invasive cancer) in 6 of 7 attempts on three radical prostatectomy specimens (patients 1532, 1535, and 1542). In addition, tissue fragments suitable for initiating three benign prostate epithelial cell lines and two benign seminal vesicle epithelial cell lines were successfully dissected from these radical prostatectomy specimens (Table 2).

Figure 1B:
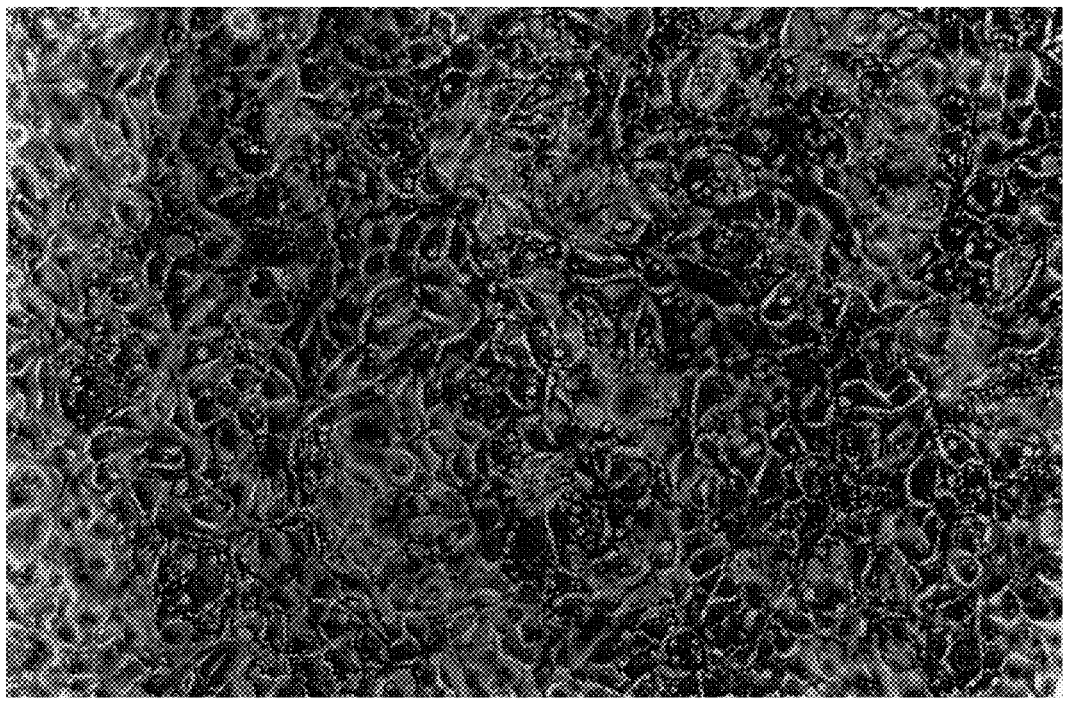

Immortalization and Immunocytochemical Characterization of Prostate-Derived Cell Lines. All but one of the 17 tissue specimens listed in Table 2 (normal prostate from patient 1519) was readily established in short-term culture. However, cell proliferation was relatively slow, and in vitro immortalization of epithelial cell cultures was necessary to establish actively growing cultures capable of surviving beyond 5–6 weeks. Adherent monolayer cultures were transduced at the second or third passage with a recombinant retrovirus encoding the E6 and E7 transforming proteins of HPV16, resulting in the establishment of 16 long-term epithelial cell lines: 4 derived from normal prostate, 2 from seminal vesicle and ten from primary tumor specimens. In addition, immortal fibroblast lines initiated from prostatic stroma in four patients were established. Successful transduction was confirmed by cell survival in G418 at a concentration of 1 mg/ml and extended cell viability and rapid proliferation beyond 50 culture passages when compared to non-immortalized cells cultured in parallel (FIG. 1A) Microscopically, all immortalized prostate epithelial cell lines exhibited a similar morphology whether derived from benign or malignant tissue, thus culture morphology was not a useful criterion for distinguishing benign from malignant cells (FIG. 1B).

To confirm the epithelial and prostatic origins of the prostate-derived cell lines, immunocytochemistry was performed on cell blocks from actively growing immortalized cultures (Table 3). Both high and low molecular weight cytokeratins were expressed by all of the epithelial cell lines initiated in our laboratory, including those derived from normal prostate, normal seminal vesicle, and prostate cancer specimens. Greater than 75% of cells stained with 4+intensity, similar to staining observed with the established metastatic prostate cancer cell lines LNCaP, DU145, PC-3 and TSU-Pr1. Thus, the epithelial origin of these cultures was confirmed. No significant cytokeratin expression was observed for control fibroblast lines or melanoma cells.

Figure 2:
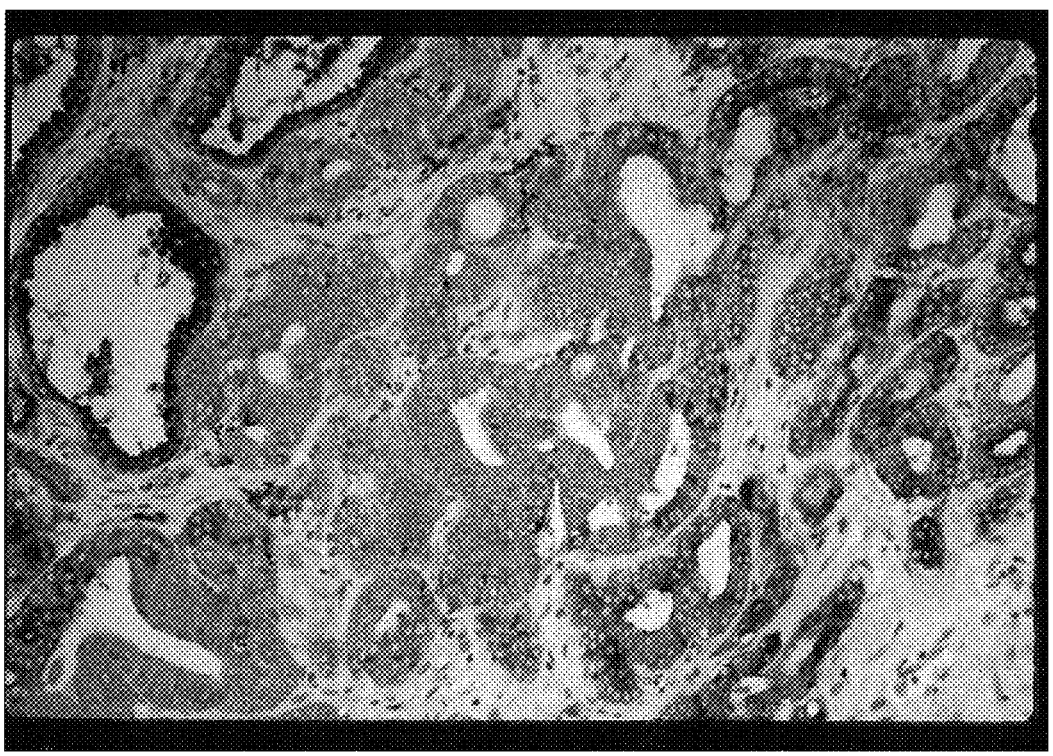
FIG. 2. Expression of PSA by benign and malignant prostate epithelial cells in situ. A paraffin-embedded tissue section from the radical prostatectomy specimen from patient 1510 contains areas of invasive prostate cancer (single arrow) as well as normal prostatic epithelium (double arrows). Dark pigmentation indicates binding of an anti-PSA monoclonal antibody. While PSA expression by normal prostatic epithelial cells is intense and homogeneous, expression by cancer cells is weak and heterogenous. Intervening stromal cells do not express PSA. (200×).

Although positive cytokeratin expression indicated that cell lines generated from primary prostate cancer specimens were in fact epithelial in origin, it was also of interest to assess expression of the prostate-associated proteins, PSA and PAP by these cultures. Only the immortalized prostate tumor-derived cell line generated from patient 1519 (1519-CPTX) expressed detectable levels of these proteins (>75% of cells staining with 2–3+intensity, and >75% with 4+intensity, respectively) following 5 culture passages. However, after 30 culture passages expression of PSA and PAP was no longer detectable in 1519-CPTX. Furthermore, expression was not inducible in late passages of this cell line by IFN-5-aza-2'-deoxycytidine or dihydroxytestosterone. Immunohistochemical examination of fixed prostate cancer tissue sections for the expression of PSA and PAP often showed weak and heterogenous staining of tumor coals, with some tumor foci demonstrating no detectable expression of these proteins. In contrast, all normal glands in the same microscopic sections stained strongly and uniformly for PSA and PAP (FIG. 2). The weak, heterogenous expression of PSA and PAP by prostate cancer cells in situ may explain the absence of expression in the immortalized prostate tumor-derived cell lines. However, lack of expression in the benign prostate epithelial cell lines does not correlate with the strong expression observed in the corresponding tissue sections, indicating that loss of PSA and PAP expression may also occur as a consequence of in vitro cell culture.

Figure 3:
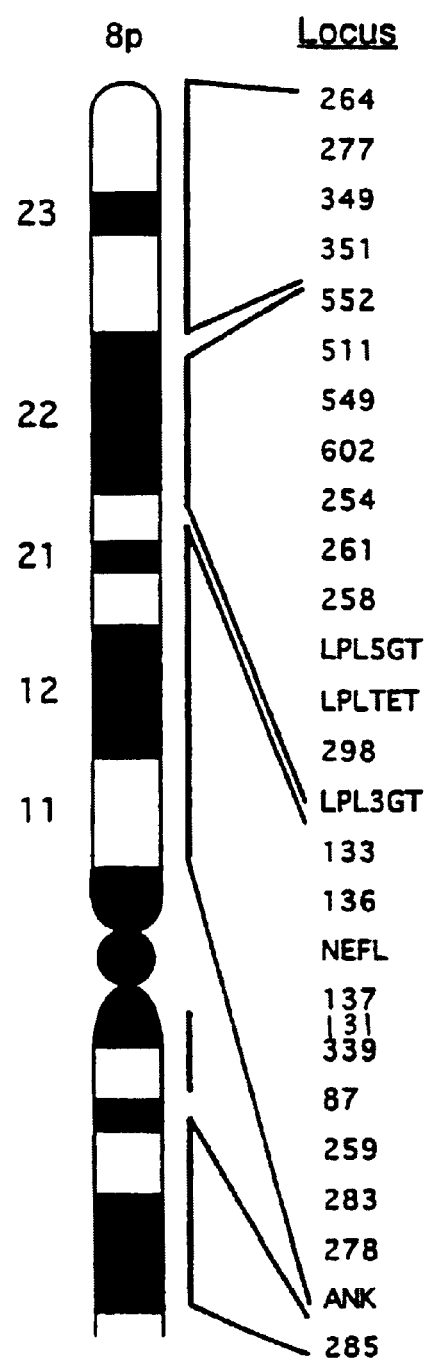
FIG. 3. Genetic map of chromosome 8p identifying the relative location of the microsatellite markers used for loss of heterozygosity analysis.

Examination of Chromosome 8p for LOH in Microdissected Tissues. As noted above, our "prostate cancer" cell lines were in most cases actually derived from tissue samples containing a mixture of benign and malignant cell types (Table 2). Since all cultures required retroviral transformation to induce long-term proliferation, and since benign and malignant transformed prostatic epithelial cells were indistinguishable on morphologic and histochemical grounds, the use of LOH analysis was investigated as an alternative means of characterizing the newly established cultures. LOH on chromosome 8p 12–21 was first assessed in microdissected foci of tumor or normal epithelial cells from the corresponding fresh tissue sections. A panel of 8 microsatellite markers, previously shown to detect a high percentage of LOH in microdissected prostate cancer specimens (19), was selected to identify chromosome 8p deletions. The panel of eight microsatellite markers are capable of identifying deletions in loci 11 through 21 of chromosome 8 as depicted in FIG. 3. Hypothesizing that microscopically normal-appearing cells might contain LOH as a precursor to malignant transformation, cryopreserved fresh autologous PBL were used as the normal control for LOH analysis. All 6 patients proved to be heterozygous (informative) at 4 or more of the 8 loci examined upon analysis of DNA from fresh PBL. However, for 2 patients (1519 and 1532), microdissected tumor specimens did not yield evidence of LOH, indicating that LOH analysis might not be useful in characterizing cell cultures derived from those specimens (Table 4).

In contrast, microdissected tumors from patients 1510 and 1512 demonstrated LOH at all examined informative loci. For patient 1535, 6 distinct microdissected foci of tumor were examined and all exhibited similar patterns of LOH. Of interest, LOH analysis of 12 distinct microdissected tumors from patient 1542 revealed different patterns to LOH, with $^{4}/_{12}$ exhibiting retention of all 16 informative alleles examined (Table 5). Microdissected normal epithelium failed to show evidence of LOH on chromosome 8p, with the exception of specimens derived from patient 1510. All 3 "normal" microdissected foci from patient 1510 exhibited extensive LOH consistent with the pattern of LOH observed in autologous tumor, emphasizing the importance of using PBL as the normal control for this type of study.

TABLE 5

LOH on chromosome 8p in Microdissected Prostate Tissues and Immortalized Cell Lines from Patient 1542

| Cell Source | Chromosome 8p Locus | | | |
|---|---|---|---|---|
| | D8S133 | D8S136 | D8S137 | D8S131 |
| Microdissected foci | | | | |
| Normal Epithelium | NL | NL | NL | NL |
| Tumor | | | | |
| 1 | LL | LL | LL | LL |
| 2 | nd | nd | NL | NL |
| 3 | LL | LL | LL | LL |
| 4 | NL | NL | NL | NL |
| 5 | LL | LL | NL | NL |
| 6 | NL | NL | NL | NL |
| 7 | LU | LU | LU | LU |
| 8 | NL | NL | NL | NL |
| 9 | LU | nd | NL | NL |

TABLE 4

LOH on chromosome 8p in Microdissected Foci of Prostate Cancer or Benign Epithelium

| Patient | No. of Foci Tested | Chromosome 8p Locus | | | | | | | |
|---|---|---|---|---|---|---|---|---|---|
| | | SFTP-2 | D8S133 | D8S136 | NEFL | D8S137 | D8S131 | D8S339 | ANK |
| 1510 | | | | | | | | | |
| tumor | 2 | ● | ● | ● | — | ● | — | ● | ● |
| normal | 3 | ● | ● | ● | — | ● | — | ● | ● |
| 1512 | | | | | | | | | |
| tumor | 1 | — | ● | ● | ● | nd | — | ● | nd |
| normal | 1 | — | ○ | ○ | ○ | nd | — | ○ | nd |
| 1519 | | | | | | | | | |
| tumor | 1 | — | ○ | ○ | ○ | — | ○ | ○ | ○ |
| normal | 1 | — | ○ | ○ | ○ | — | ○ | ○ | ○ |
| 1532 | | | | | | | | | |
| tumor | 8 | — | ○ | ○ | ○ | nd | — | ○ | nd |
| normal | 1 | — | ○ | ○ | ○ | nd | — | ○ | nd |
| 1535 | | | | | | | | | |
| tumor | 6 | ● | ● | ● | ● | — | ● | ○ | — |
| normal | 1 | ○ | ○ | ○ | ○ | — | ○ | ○ | — |

Retention of heterozygosity (○)
Loss of heterozygosity (●)
Not informative (Homozygous alleles) (—)
Not determined (nd)

TABLE 5-continued

LOH on chromosome 8p in Microdissected Prostate Tissues and Immortalized Cell Lines from Patient 1542

| Cell Source | | Chromosome 8p Locus | | | |
|---|---|---|---|---|---|
| | | D8S133 | D8S136 | D8S137 | D8S131 |
| 10 | | LL | LL | NL | NL |
| 11 | | LU | LL | NL | NL |
| 12 | | NL | LL | LL | NL |
| Cultured Cell Lines | | | | | |
| NPTX | (p20)[a] | NL | NL | NL | NL |
| CP$_3$TX | (p3,6,13) | NL | NL | NL | NL |
| CP$_3$TX | | | | | |
| clone 1[d] | (p8) | LL | LL | nd | LL |
| clone 3[b] | (p8) | nd | NL | nd | NL |
| clone 4[e] | (p8) | LU | LU | nd | LU |
| CP$_3$TX | (p21) | LU | LU | LU | LU |
| CP$_3$TX clone[c] | (p23) | LU | LU | LU | LU |

No LOH (NL)
Loss of the upper allele (LU)
Loss of the lower allele (LL)
Not determined (nd)
[a]Number of sequential culture passages.
[b]Representative of 7 individual clones.
[c]Representative of 30 individual clones.
[d]Clone 1542-CP$_3$TX.8.1
[e]Clone 1542-CP$_3$TX.8.4

LOH Analysis of Immortalized Cell Lines from Patient 1542.

Figure 4:
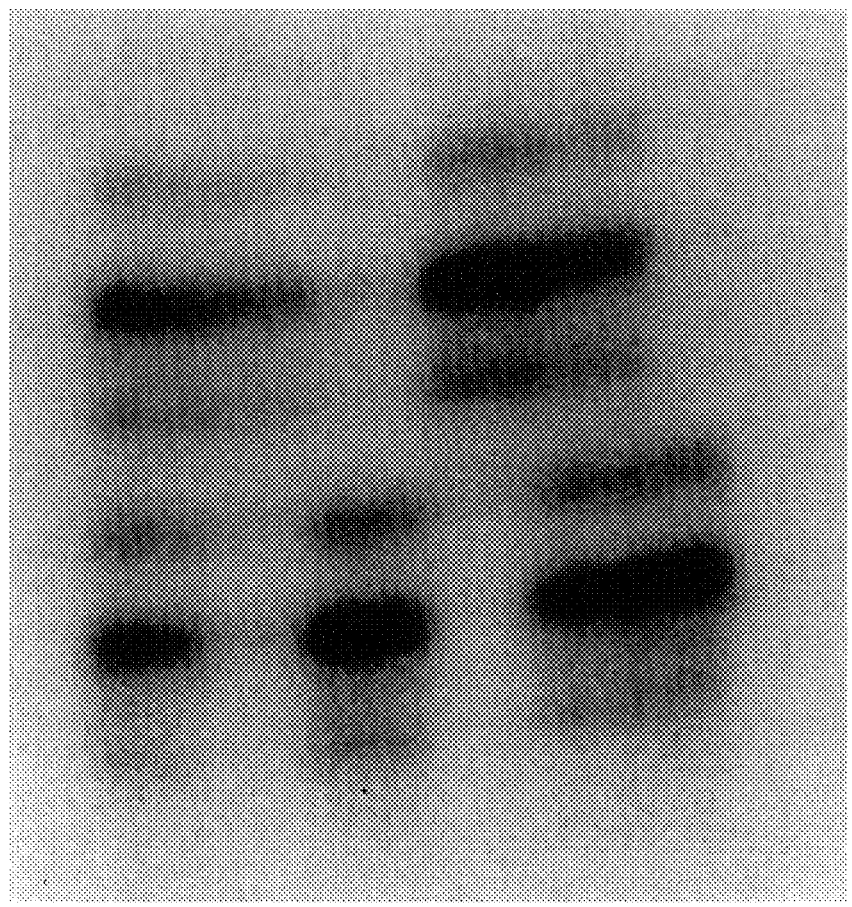
FIG. 4. PCR analysis of microsatellite D8S136 on fresh and cultured cells from patient 1542. Lane 1, 1542-NPTX, passage 26. Lane 2, fresh microdissected tumor #11. Lane 3, uncloned 1542-CP$_3$TX$_1$ passage 21. Lanes 4–6, tumor clones 1542-CP$_3$TX.8.1, 1542-CP$_3$TX.8.3 and 1542-CP$_3$TX.8.4, derived from the 8th passage of 1542-CP$_3$TX.

Loss of heterozygosity in cell cultures generated from patient 1542 was of special interest in light of the diverse patterns of LOH manifested in 12 distinct microdissected tumor foci. This patient was informative at D8S133, D8S136, D8S137, D8S131, D8S339 and ANK. Four of those loci were closely examined for allelic loss in cultures derived from tumor, normal prostate, normal seminal vesicle, and normal fibroblasts (Table 5). Repeated analysis of early passage bulk cultures (passage 3, 6, 13) derived from tumor, designated 1542-CP$_3$TX, failed to reveal LOH for any of the four microsatellite markers examined. However, after 21 serial culture passages (approximately 6 months), 1542-CP$_3$TX exhibited loss of the upper allele at all four loci examined. This pattern of loss was identical to that found in microdissected tumor focus #7. Thirty single cell clones were generated from passage 23 of 1542-CP$_3$TX, and all demonstrated a pattern of LOH identical to that of the uncloned late passage culture and microdissected tumor #7, suggesting the clonal or near clonal composition of the bulk late-passage cell line. These findings also suggested that the failure to detect LOH in early passages of 1542-CP$_3$TX might reflect the presence of multiple tumor clones in the bulk culture having different patterns of LOH, which would preclude the detection of LOH with a PCR-based technique. To investigate this, single cell clones were generated from an early passage (passage 8) of 1542-CP$_3$TX and examined for LOH (FIG. 4). Seven of nine clones did not manifest LOH at D8S136 or D8S131, similar to 3/12 microdissected tumors from patient 1542. However, a single clone (clone 4) (1542-CP$_3$TX.8.4) exhibited a pattern of LOH similar to that of microdissected tumor # 7, the late passage of 1542-CP$_3$TX and its derivative clones, indicating that the tumor clone(s) that dominated the late passage bulk culture apparently resided in very early culture passages. Of interest, clone 1 (1542-CP$_3$TX.8.1) from the early passage 1542-CP$_3$TX exhibited a different pattern of LOH than that observed for the other 8 early passage clones, with loss of the lower alleles of D8S133, D8S136, and D8S131. This was again consistent with the pattern of LOH detected in two microdissected tumors (#1 and #3). It is important to note that LOH was not detected in repeated experiments with early and late passages of immortalized cultured normal prostatic epithelium, seminal vesicle, or fibroblasts from patient 1542, arguing against the likelihood that the LOR observed in cells derived from tumor was a culture artifact.

Examination of LOH of Chromosome 8p12–21 in Cell Cultures Derived from the Five Remaining Patients.

In patients 1510 and 1512, IOH was detected at multiple loci in microdissected tumor specimens (Table 4). However, immortalized epithelial cultures generated from corresponding cancer-containing tissue specimens failed to manifest LOH when examined on a bulk level at early or late culture passages. Likewise, clones grown from late culture passages (passage 23 for 1510-CPTX, passage 31 for 1512-CPTX) failed to show evidence of LOH. This may reflect the presence of significant amounts of normal prostatic epithelium in the tissue specimens from which these cultures were generated (Table 2), with overgrowth of normal cells in vitro. Cloning these cell lines at very early culture passages may yield more rewarding results.

Examination of microdissected tumor foci from patients 1519 (one focus) and 1532 (8 foci) failed to reveal LOH (Table 4). Nevertheless, cultures established from these tumors were assessed for LOH. In the case of patient 1519, examination of the bulk culture 1519-CPTX showed retention of heterozygosity at 6 informative loci which were examined. However, among 11 single cell clones derived from culture passage 24 one showed LOH at a single locus, D8S133. In the case of patient 1532, the bulk-cultured line 1532-CP$_2$TX, generated from one of two tumor specimens procured (Table 2), showed LOH at D8S133, D8S136 and NEFL but only after prolonged culture (passage 24). All 10 clones generated from the late culture passage also showed the same pattern of loss. However, an immortalized culture derived from normal prostate tissue from patient 1532 failed to show evidence of LOH even after 20 culture passages. Likewise, an autologous immortalized fibroblast line retained heterozygosity at the same 3 alleles which were lost in 1532-CP$_2$TX. Thus, the LOH observed in a single 1519-CPTX clone and in 1532-CP$_2$TX suggests that these findings may reflect LOH existing in an in situ tumor focus which was not dissected for analysis.

Interesting results were obtained with cultures derived from patient 1535. In this case, extensive LOH was documented in 6 separate microdissected tumor foci, all showing the same pattern of loss (Table 4). Early and late passage cultures generated from prostate cancer, as well as from normal prostate and normal seminal vesicle, failed to show LOH. Likewise, 11 tumor clones generated at culture passage 27 failed to show loss. However, cloning of an early passage tumor culture (passage 12) revealed one clone with a pattern of LOH matching the 6 microdissected tumor foci (clone 1535-CP$_1$TX.14.3). These results recapitulate those observed with patient 1542 and argue that early cloning of immortalized cultures generated from histologically heterogenous prostate cancer specimens may be needed to obtain pure tumor cultures.

Expression of MHC Molecules by Immortalized Cell Lines Derived from Prostate Cancer.

Examination of surface MHC expression on immortalized tumor-derived cell lines was of importance in considering the potential usefulness of these lines for immunologic studies. Cultures derived from all 6 patients expressed significant surface levels of MHC class I and the adhesion molecule ICAM-1 as determined by flow cytometry (Table 6).

TABLE 6

Cell Surface Expression of MHC and Adhesion Molecules by Immortalized Prostate Epithelial Cell Lines

| | | % Positive Cells | | |
|---|---|---|---|---|
| Patient # | Cell Source | MHC class I | MHC class II | ICAM-1 |
| 1510 | F | 96 | 1 | 57 |
| | CP | 90 | 2 | 22 |
| 1512 | NP | 100 | 10 | 43 |
| | CP | 97 | 6 | 35 |
| 1519 | CP | 92 | 3 | 40 |
| 1532 | NP | 88 | 1 | 50 |
| | CP1 | 89 | 4 | 65 |
| | CP2 | 95 | 1 | 74 |
| 1535 | NP | 78 | 0 | 44 |
| | SV | 96 | 1 | 80 |
| | CP1 | 99 | 1 | 60 |
| | CP2 | 82 | 1 | 50 |
| 1542 | F | 87 | 1 | 58 |
| | NP | 63 | 2 | 65 |
| | SV | 69 | 1 | 87 |
| | CP1 | 71 | 1 | 66 |
| | CP2 | 72 | 1 | 73 |
| | CP3 | 40 | 3 | 64 |

Figures 5A, 5B, 5C, 5D, 5E, 5F:
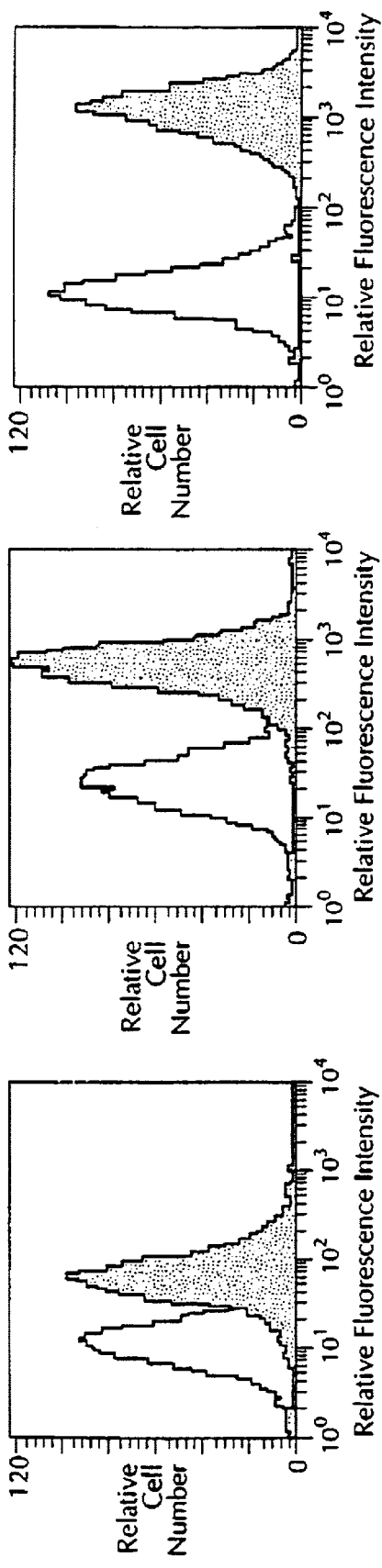
FIGS 5A–5F. IFN-γ induces enhanced surface expression of MHC class I and II molecules on 1542-CP$_3$TX. Untreated 1542-CP$_3$TX cells expressed a moderate amount of class I molecules (staining with mAb W6/32) (5A) but did not express detectable amounts of class II molecule (mAb L243) (5B). After exposure to IFN-γ500 U/ml for 3 days, class I expression was enhanced (5C), and class II expression was induced (5D). MHC expression by autologous EBV-transformed B cells is shown for comparison (5E and 5F).

None of the immortalized lines expressed detectable levels of either MHC class II or the B7 family of co-stimulatory molecules (B7.1, B7.2). However, it was of interest to determine if the expression of MHC molecules could be up-regulated in the presence of IFN-γ, as has been reported previously for melanoma cell lines (29). Immortalized tumor derived cell lines 1532-CP$_2$TX, 1535-CP$_1$TX, and 1542-CP$_3$TX were cultured in the presence of 500 U/ml IFN-γ for 72 h and then assessed for MHC expression. All were induced to express significant amounts of MHC class II molecules. In addition, MHC class I molecule expression was enhanced when compared to untreated controls (FIG. 5C vs. 5A). In this light, these immortalized tumor-derived cell lines represent potentially valuable reagents for studying or stimulating CD4$^+$ and CD8$^+$ cell-mediated immune responses in patients with primary adenocarcinoma of the prostate.

HLA Typing of Prostate Epithelial Cell Lines. HLA typing was conducted for each patient from which prostate epithelial cell lines were derived. A, B and C types were determined by serotyping lymphocytes using methods known in the art. DR and DQ types were determined by genotyping lymphocytes using standard methods. The results of the HLA typing are provided in Table 7.

TABLE 7

HLA Types of Prostate Epithelial Cell Lines

| Patient Number | A | B | Cw | DRB1* | DQB1* | DRB |
|---|---|---|---|---|---|---|
| 1510 | 29,31 | 44,60 | 3,— | 0401,07 | 0201,0302 | 4*0101 |
| 1512 | 3,— | 7,— | 7,— | 1501,— | 0602,— | 5*0101 |
| 1519 | 24,32 | 14,44 | 5,8 | 0701,1301 | 0201,0603 | 3*0101, 4*0101 |
| 1532 | 1,— | 8,57 | 6,7 | 0301,04 | 0201,0301 | 3*0101, 4*0101 |
| 1535 | 1,31 | 7,37 | 6,7 | 07,04 | 0201,0302 | 4*0101 |
| 1542 | 1,23 | 50,70 | 2,— | 0301,1101 | 0201,0301 | 3*0202 |

REFERENCES

1. Parker, S. L., Tong, T., Bolden, S., and Wingo, P. A. Cancer Statistics, 1996. *CA Cancer J. Clin.*, 65: 5–27, 1996.

2. Isaacs, J. T., Isaacs, W. B., and Schalken, J. Comparative aspects of multistep prostatic carcinogenesis in humans and rodents. *Prog. Clin. Biol. Res.*, 376: 261–288, 1992.

3. Webber, M. M., Chaproniere-Rickenberg, D. M., and Donohue, R. E. Isolation and growth of adult human protatic epithelium in serum-free, defined medium. In: Methods for serum-free culture of cells of the endocrine system, pp. 47–61. New York: Alan R. Liss, 1984.

4. Peehl, D. M. Culture of human prostatic epithelial cells. In: Culture of epithelial cells, pp. 159–180. New York: Wiley-Liss, 1992.

5. Rhim, J. S., Webber, M. M., Bello, D., Lee, M. S., Arnstein, P., Chen. L., and Jay, G. Stepwise immortalization and transformation of adult human prostate epithelial cells by combination of HPV-18 and v-Ki-ras. *Proc. Natl. Acad. Sci. USA.* 91: 11874–11878, 1994.

6. Bondou, P., Cussenot, O., Soliman, H., Villette, J. M., Teillac, P., LeDuc, A., and Fiet, J. Distinct androgen 5 alpha-reduction pathways in cultured fibroblasts and immortalized epithelial cells from normal human adult prostate. *J. Urol.*, 152: 226–231, 1994.

7. Lee, M., Garkovenko, E., Yun, J. S., Weijerman, P. C., Peehl. D. M., Chen. L., and Rhim, J. S. Characterization of adult human prostatic epithelial cells immortalized by polybrene-induced DNA transfection with a plasmid containing an origin-defective SV40 genome. *Int. J. Oncol.*, 4: 821–830, 1994.

8. Weijerman, P. C., König J. J., Wong, S. T., Niesters, G. M., and Peehl, D. M. Lipofection-mediated immortalization of human prostatic epithelial cells of normal and malignant origin using human papillomavirus type 18 DNA. *Cancer Res.*, 54: 5579–5583, 1994.

9. Brothman, A. R., Peehl, D. M., Patel, A. M., and McNeal, J. E. Frequency and pattern of karyotypic abnormalities in human prostate cancer. *Cancer Res.*, 50: 3795–3803, 1990.

10. Brothman, A. R., Peehl, D. M., Patel, A. M., MacDonald, G. R., McNeal, J. E., Ladaga, L. E., and Schellhammer, P. F. Cytogenetic evaluation of 20 cultured primary prostatic tumors. *Cancer Genet. Cytogenet.*, 55: 79–84, 1991.

11. Brothman, A. R., Patel. A. M., Peehl. D. M., and Schellhammer, P. F. Analysis of prostatic tumor cultures using fluorescence in-situ hybridization (FISH). *Cancer Genet. Cytogenet.*, 62: 180–185, 1992.

12. Isaacs, W. B., Bova, G. S., Morton, R. A., Bussemakers, J. D., and Ewing, C. M. Molecular biology of prostate cancer. *Seminars in Oncology*, 21: 514–521, 1994.

13. Carter, B. S., Ewing, C. M., Ward, W. S., Treiger, B. F., Aalders, T. W., Schalken, J. A., Epstein, J. I., and Isaacs, W. B. Allelic loss of chromosomes 16q and 10q in human prostate cancer. *Proc. Natl. Acad. Sci. USA.* 87: 8751–8755, 1990.

14. Bergenheim, U. S. R., Kunimi, K., Collins. V. P., and Ekman, P. Deletion mapping of chromosomes 8, 10, and 16 in human prostatic carcinoma. *Genes, Chromosomes and Cancer*, 3: 215–220, 1991.

15. Sakar, W. A., Macoska, J. A., Benson, P., Grignon, D. J., Wolman, S. R., Pontes, J. E., and Crissman, J. D. Allelic loss in locally metastatic, multisampled prostate cancer. *Cancer Res.*, 54: 3273–3277, 1994

16. Bova, G. S., Carter, B. S., Bussemakers, M. J. G., Emi, M., Fujiwara, Y., Kyprianou, N., Jacobs, S. C., Robinson, J. C., Epstein, J. I., Walsh, P. C., and Isaacs, W. B. Homozygous deletion and frequent allelic loss of chromosome 8p22 loci in human prostate cancer. *Cancer Res.*, 53: 3869–3873, 1993.

17. Trapman, J., Sleddens. H. F. B. M., van der Weiden, M. M., Dinjens, W. N. M., Konig, J. J., Schroder, F. H., Faber, P. W., and Bosman, F. T. Loss of heterozygosity of chromosome 8 microsatellite loci implicates a candidate tumor suppressor gene between the loci D8S87 and D8S133 in human prostate cancer. *Cancer Res.*, 54: 6061–6064, 1994.

18. Macoska, J. A., Trybus, T. M., Benson, P. D., Sakr, W. A., Grignon, D. J., Wojno, K. D., Pietruk, T., and Powell, I. J. Evidence for three tumor suppressor gene loci on chromosome 8p in human prostate cancer. *Cancer Res.*, 55: 5390–5395, 1995.

19. Vocke, C. D., Pozzatti, R. O., Bostwick, D. G., Florence, C. D., Jennings, S. B., Strup, S. E., Duray, P. H., Liotta, L. A., Emmert-Buck, M. R., and Linehan, W. M. Analysis of 99 microdissected prostate carcinomas reveals a high frequency of allelic loss on chromosome 8p12–21. *Cancer Res.*, 56: 2411–2416, 1996.

20. Emmert-Buck, M. R., Vocke, C. D., Pozzatti, R. O., Duray, P. H., Jennings, S. B., Florence, C. D., Zhuang, Z., Bostwick, D. G., Liotta, L. A., and Linehan, W. M. Allelic loss on chromosome 8p12–21 in microdissected prostatic intraepithelial neoplasia. *Cancer Res.*, 55: 2959–2962, 1995.

21. Topalian, S. L., Muul, L. M., Solomon. D., and Rosenberg, S. A. Expansion of human infiltrating lymphocytes for use in immunotherapy trials. *J. Immunol. Meth.*, 102: 127–141, 1987.

22. Halbert, C. L., Demers, G. W., and Galloway, D. A. The E7 gene of human papillomavirus type 16 is sufficient for immortalization of human epithelial cells. *J. Virol.*, 65: 473–478. 1991.

23. Topalian, S. L., Solomon, D., Avis, F. P., Chang, A. E., Freerksen, D. L., Linehan, W. M., Lotze, M. T., Robertson. C. N., Seipp, C. A., Simon, P., Simpson, C. G., and Rosenberg, S. A. Immunotherapy of patients with advanced cancer using tumor-infiltrating lymphocytes and recombinant interleukin-2: A pilot study. *J. Clin. Oncol.*, 6: 839–853, 1988.

24. Emmert-Buck, M. R., Roth, M. J., Zhuang, Z., Campo, E., Rozhin, J., Sloane, B. F., Liotta, L. A., Stetler-Stevenson, W. G. Increased gelatinase A and cathepsin B activity in invasive tumor regions of human colon cancer samples. *Am. J. Pathol.*, 154: 1285–1290, 1994.

25. Zhuang, Z., Bertheau, P., Emmert-Buck, M. R., Liotta, L. A., Gnarra. J., Linehan, W. M., Lubensky, I. A. A new microdissection technique for archival DNA analysis of specific cell populations in lesions less than one millimeter. *Am. J. Pathot.*, 146: 620–625, 1995.

26. Zhuang, Z., Merino. M. J., Chuaqui, R., Liotta. L. A., and Emmert-Buck. M. R. Identical allelic loss on chromosome 11q13 in microdissected in situ and invasive human breast cancer. *Cancer Res.*, 55: 467–471, 1995.

27. Hung, T., Mak, K., and Fong, K. A. A specificity enhancer for polymerase chain reaction. *Nucleic Acid Res.*, 18: 4953, 1990.

28. Litt, M., Hauge, X., and Sharma, V. Shadow bands seen when typing polymorphic dinucleotide repeats: some causes and cures. *Biotechniques*, 15: 280–284, 1993.

29. Markus, N. R., Rosenberg, S. A., and Topalian. S. L. Analysis of cytoldne secretion by melanoma-specific CD4+T lymphocytes. *J. Interferon Cytokine Res.*, 15: 739–746, 1995.

30. Burrows, M. T., Buns, J. E, and Suzuki, Y. Studies on the growth of cells. The cultivation of bladder and prostaucic tumors outside the body. *J. Urol.* 1: 3, 1917.

31. Horoszewicz, J. S., Leong, S. S., Kawinski, E., Karr, J. P., Rosentbal, H., Chu, T. M., Mirand, E. A., and Murphy, G. P. LNCaP model of prostatic carcinoma. *Cancer Res.*, 43: 1809–1818, 1983.

32. Henttu, P., Liao, S., and Vihko, P. Androgens up-regulate the human prostate specific antigen messenger ribonucleic acid (mRNA), but down-regulate the prostatic acid phosphatase mRNA in the LNCaP cell line. *Endocrinology*, 130: 766–772, 1992.

33. Cooney, E. L. et al 1991 *lancet* Vol. 337:567.

34. Wolff, J. A. et al 1990 *Science* Vol. 247:1465.

35. Davis, H. L. et al 1993 *Hum. Gene Ther.* Vol. 4:151.

36. Yang, N. S. et al 1990 *Proc. Natl. Acad. Sci USA* Vol. 87:9568.

37. Williams, R. S. et al 1991 *Proc. Nat'l Acad. Sci USA* Vol. 88:2726.

38. Fynan, E. R. et al 1995 *Proc. Natl. Acad. Sci USA* Vol. 90:11478.

39. Eisenbraum, M. D. et al 1993 *DNA and Cell Biol.* Vol 12:791.

40. Fuller, D. H. et al 1994 *AIDS Res. Hum. Retrovir.* Vol 10(11):1433.

41. Acsadi, G. et al 1991 *Nature* Vol. 352:815.

42. Matteucci, M. D. et al 1996, *Nature* vol. 384:20–22.

43. Perkus et al *Science* 1985 Vol. 229:981–984.

44. Kaufman et al *Int. J. Cancer* 1991, Vol. 48:900–907.

45. Moss *Science* 1991 Vol. 252:1662.

46. Smith and Moss *BioTechnigues* Nov/Dec 1984, p. 306–312.

47. U.S. Pat. No. 4,738,846.

48. Sutter and Moss *Proc. Nat'l Acad. Sci USA* 1992 Vol. 89:10847–10851.

49. Baxby and Paoletti *Vaccine* 1992 Vol. 10:8–9.

50. PCT International Publication No. WO09/16716 published Aug. 4, 1994.

51. *Short Protocols in Molecular Biology*, 3rd ed. F. Ausubel et al, eds. John Wiley & Son, Inc., 1995.

52. *Basic Methods in Molecular Biology*, 2nd ed. L. Davis et al, eds. Appleton & Lange, 1994.

We claim:

1. A cloned, immortalized, malignant prostate epithelial cell line 1535-CP$_1$TX.14.3 deposited as ATCC CRL-12263 with the ATCC.

2. A cloned, immortalized, malignant prostate epithelial cell line 1542-CP$_3$TX.8.4 deposited as ATCC CRL-12264 with the ATCC.

3. A cloned, immortalized, malignant prostate epithelial cell line 1542-CP$_3$TX.8.1 deposited as ATCC CRL-12265 with the ATCC.

4. An immortalized malignant, human, adult prostate epithelial-cell line 1532-CP2TX deposited as CRL-12038 with ATCC.

5. An immortalized, malignant, human, adult prostate epithelial cell line 1535-CP$_1$TX deposited as CRL-1241 with the ATCC.

6. An immortalized, malignant, human adult prostate epithelial cell line 1542-CP$_1$TX deposited as CRL 12037 with the ATCC.

7. An immortalized, malignant prostate epithelial cell line 1510-CPTX deposited as ATCC PTA-604 with the ATCC, wherein the HLA type of the cell line comprises HLA-A29, HLA-A31, HLA-B44, HLA-B60, HLA-Cw3, HLA-DRB1*0401, HLA. DRB1*07, HLA-DQB1*0201, HLA-DQB1*0302, and HLA-DRB4*0101.

8. An immortalized, malignant prostate epithelial cell line 1512-CPTX deposited as ATCC PTA-605 with the ATCC, wherein the HLA type of the cell line comprises HLA-A3, HLA-B7, HLA-Cw7, HLA-DRB1*1501, HLA-DQB1*0602, and HLA-DRB5*0101.

9. An immortalized, malignant prostate epithelial cell line 1519-CPTX deposited as ATCC PTA-606 with the ATCC.

10. A composition comprising an immortalized, human, adult, malignant, prostate epithelial cell line, clone, or lysed cell thereof according to claim 1–6, 7, 8, or 9, and a pharmaceutically acceptable carrier.

11. The composition according to claim 10 further comprising an adjuvant, costimulatory molecule, cytokine, chemokine, adhesion molecule or combination thereof.

12. An immunogen for eliciting an immune response comprising an immortalized, human, adult, malignant, prostate epithelial cell line, clone or lysed cell thereof, according to claims 1–6, 7, 8, or 9.

13. The immunogen according to claim 9 further comprising an adjuvant, cytokine, costimulatory molecule, chemokine, adhesion molecule or combination thereof.

14. The immunogen according to claim 12, wherein the immune response is a cell mediated response.

15. The immunogen according to claim 12, wherein the immune response is humoral response.

16. A kit comprising at least one immortalized, adult, malignant, prostate epithelial cell line according to claims 1–6, or lysed cell thereof.

17. A kit comprising at least one immortalized adult, malignant, prostate epithelial cell line according to claims 14–16, or lysed cell thereof.

18. A kit according to claim 16, further comprising an adjuvant.

19. A kit according to claim 16 further comprising a cytokine, costimulatory molecule, chemokine, adhesion molecule, or combination thereof.

20. A kit according to claim 17, further comprising an adjuvant.

21. A kit according to claim 17 further comprising a cytokine, costimulatory molecule, chemokine, adhesion molecule, or combination thereof.

* * * * *